(12) United States Patent
Ren et al.

(10) Patent No.: US 9,403,820 B2
(45) Date of Patent: Aug. 2, 2016

(54) KINASE INHIBITOR POLYMORPHS

(71) Applicant: INTELLIKINE LLC, La Jolla, CA (US)

(72) Inventors: Pingda Ren, San Diego, CA (US); Michael Martin, San Marcos, CA (US); Christopher Peter Worrall, Cheshire (GB); Susanna del Rio Gancedo, Cambridgeshire (GB)

(73) Assignees: Intellikine LLC, La Jolla, CA (US); Sigma-Aldrich Company Limited (GB)

( * ) Notice: Subject to any disclaimer, the term of this patent is extended or adjusted under 35 U.S.C. 154(b) by 182 days.

(21) Appl. No.: 14/357,144

(22) PCT Filed: Nov. 12, 2012

(86) PCT No.: PCT/US2012/064729
§ 371 (c)(1),
(2) Date: Jan. 22, 2015

(87) PCT Pub. No.: WO2013/071272
PCT Pub. Date: May 16, 2013

(65) Prior Publication Data
US 2015/0005301 A1     Jan. 1, 2015

Related U.S. Application Data

(60) Provisional application No. 61/558,962, filed on Nov. 11, 2011.

(51) Int. Cl.
C07D 471/04     (2006.01)

(52) U.S. Cl.
CPC ........... *C07D 471/04* (2013.01); *C07B 2200/13* (2013.01)

(58) Field of Classification Search
CPC .................. C07D 471/04; C07B 2200/13
USPC .......................................... 546/121; 514/300
See application file for complete search history.

(56) References Cited

U.S. PATENT DOCUMENTS

| 4,450,164 | A | 5/1984 | Bristol et al. |
|---|---|---|---|
| 9,085,560 | B2 * | 7/2015 | Ren ..................... C07D 401/14 546/121 |
| 2004/0023972 | A1 | 2/2004 | Sundermann et al. |
| 2008/0090835 | A1 | 4/2008 | Koltai et al. |
| 2009/0312319 | A1 | 12/2009 | Ren et al. |
| 2010/0184760 | A1 | 7/2010 | Ren et al. |
| 2011/0046165 | A1 | 2/2011 | Ren et al. |

FOREIGN PATENT DOCUMENTS

| WO | 2007036732 A1 | 4/2007 |
|---|---|---|
| WO | 2011022439 A1 | 2/2011 |

OTHER PUBLICATIONS

CID 50991428—Compound Summary by PubChem Apr. 4, 2011 available at http://pubchem.ncbi.nlm.nih.gov/summary/summary.cgi?cid=50991428; accessed on Jan. 25, 2012.

* cited by examiner

*Primary Examiner* — Jennifer M Kim
(74) *Attorney, Agent, or Firm* — Honigman Miller Schwartz and Cohn LLP; Lucy X. Yang; Jonathan P. O'Brien

(57) ABSTRACT

Polymorphs of chemical compounds that modulate kinase activity, including PI3K activity, and chemical compounds, pharmaceutical compositions, and methods of treatment of diseases and conditions associated with kinase activity, including PI3K activity, are described herein.

9 Claims, 15 Drawing Sheets

KINASE INHIBITOR POLYMORPHS

CROSS-REFERENCE TO RELATED APPLICATIONS

This application claims the benefit of priority U.S. Provisional Patent Application No. 61/558,962 filed Nov. 11, 2011; entitled, "Kinase Inhibitor Polymorphs," which is fully incorporated herein by reference for all purposes.

BACKGROUND OF THE INVENTION

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids within cells. These enzymes, and the resulting phosphorylated lipids and lipid-derived biologically active organic molecules, play a role in many different physiological processes, including cell proliferation, migration, adhesion, and differentiation. A particular group of lipid kinases comprises membrane lipid kinases, i.e., kinases that catalyze the phosphorylation of lipids contained in or associated with cell membranes. Examples of such enzymes include phosphinositide(s) kinases (such as PI3-kinases, PI4-Kinases), diacylglycerol kinases, and sphingosine kinases.

The phosphoinositide 3-kinases (PI3Ks) signaling pathway is one of the most highly mutated systems in human cancers. PI3K signaling is involved in many other disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation (Katso et al., 2001). The class I PI3Ks (p110α, p110β, p110δ, and p110γ) are typically activated by tyrosine kinases or G-protein coupled receptors to generate PIP3, which engages downstream effectors such as those in the pathways of Akt/PDK1, mTOR, the Tec family kinases, and the Rho family GTPases. The class II and III PI3-Ks play a key role in intracellular trafficking through the synthesis of PI(3)P and PI(3,4)P$_2$.

The alpha (α) isoform of PI3K has been implicated, for example, in a variety of human cancers. Angiogenesis has been shown to selectively require the a isoform of PI3K in the control of endothelial cell migration. (Graupera et al, Nature 2008; 453; 662-6). Mutations in the gene coding for PI3K α or mutations which lead to upregulation of PI3K α are believed to occur in many human cancers such as lung, stomach, endometrial, ovarian, bladder, breast, colon, brain and skin cancers. Often, mutations in the gene coding for PI3K α are point mutations clustered within several hotspots in helical and kinase domains, such as E542K, E545K, and H1047R. Many of these mutations have been shown to be oncogenic gain-of-function mutations. Because of the high rate of PI3K a mutations, targeting of this pathway may provide valuable therapeutic opportunities. While other PI3K isoforms such as PI3K δ or PI3K γ are expressed primarily in hematopoietic cells, PI3K α, along with PI3K β, is expressed constitutively.

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, autoimmune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and autoimmune diseases such as lupus.

Downstream mediators of the PI3K signal transduction pathway include Akt and mammalian target of rapamycin (mTOR). Akt possesses a pleckstrin homology (PH) domain that binds PIP3, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family. mTOR has been implicated in a wide range of biological processes including cell growth, cell proliferation, cell motility and survival. Disregulation of the mTOR pathway has been reported in various types of cancer. mTOR is a multifunctional kinase that integrates growth factor and nutrient signals to regulate protein translation, nutrient uptake, autophagy, and mitochondrial function.

Dysregulation of signaling pathways mediated by many other kinases is a key factor in the development of human diseases. Aberrant or excessive protein kinase activity or expression has been observed in many disease states including benign and malignant proliferative diseases, disorders such as allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

As such, kinases particularly lipid kinases such as PI3Ks and protein kinases such as mTor are prime targets for drug development. While compounds with inhibitory activity of such targets are often initially evaluated for their activity as a solution, solid state characteristics such as polymorphism and salt form are also important. Polymorphic forms or salt forms of a drug substance such as an inhibitor of PI3Ks can have different chemical and physical properties, including melting point, chemical reactivity, apparent solubility, dissolution rate, optical and mechanical properties, vapor pressure, and density. These properties can have a direct impact on the ability to process or manufacture a drug substance and the drug product. Moreover, differences in these properties can and often lead to different pharmacokinetics profiles for different polymorphic forms or salt forms of a drug. Therefore, polymorphism and salt form are often very important factors under regulatory review of the 'sameness' of drug products from various manufacturers. For example, polymorphism has been evaluated in many multi-million dollar and even multi-billion dollar drugs, such as warfarin sodium, famotidine, and ranitidine. Polymorphism and salt form can affect the quality, safety, and/or efficacy of a drug product, such as a kinase inhibitor.

Thus, there still remains a need for polymorphs and salt forms of inhibitors of PI3Ks, as well as lipid kinases such as mTor and/or Akt. This invention addresses this need and provides related advantages as well.

SUMMARY OF THE INVENTION

In one embodiment, the invention is directed to a method of making a pharmaceutically-acceptable polymorph of a compound of Formula I:

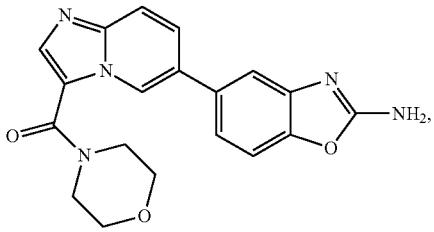 [SMILES: Nc1nc2cc(-c3ccc4ncc(C(=O)N5CCOCC5)n4c3)ccc2o1]

said method comprises (i) suspending or dissolving the compound of Formula I in an organic solvent system; (ii) adding an acid to said suspension or solution to result in a mixture; (iii) subjecting said mixture to at least one heating and cooling cycle; and (iv) isolating said polymorph. In various embodiments, the organic solvent system includes methanol, ethanol, THF, nitromethane, acetonitrile, methylethyl ketone (MEK), ethyl acetate, 1,4-dioxane, dichloromethane, DMSO, methyl t-butyl ether (MTBE), isopropyl alcohol (IPA), acetone, N-methyl pyrrolidone (NMP), butyl acetate, or toluene. In one embodiment, the organic solvent system is an organic solvent which is nitromethane, THF, methylethyl ketone (MEK), or acetonitrile. In various embodiments, the acid may include naphthalene sulfonic acid, naphthalene disulfonic acid, L-aspartic acid, p-toluenesulfonic acid, ethane-1,2-disulfonic acid (EDSA), hydrochloric acid (HCl), hydrobromic acid (HBr), citric acid, 2-hydroxyethanesulfonic acid, fumaric acid, sulfuric acid, maleic acid, methanesulfonic acid (MSA), phosphoric acid, or oxalic acid. In one embodiment, the acid is hydrochloric acid (HCl) or hydrobromic acid (HBr). In various embodiments, the concentration of HCl may be from 0.1-5.0 M. In a further embodiment, the concentration of HCl is 1.0 M in THF. In various embodiments, the concentration of HBr may be from 0.1-5.0 M. In a further embodiment, the concentration of HBr is 1.0 M in THF. In various embodiments, the heating cycle may start between −5° C. and 30° C. In various embodiments, the cooling cycle may start between 40° C. and 100° C. In one embodiment, the heating and cooling cycle is carried out between 25° C. and 50° C. In various embodiments, the heating or cooling cycle may be ramped at 0.1-10° C.·min$^{-1}$. In one embodiment, the heating or cooling cycle is ramped at 1° C.·min$^{-1}$. In various embodiments, the heating or cooling cycle may last from 1 hour to 10 weeks.

The pharmaceutically-acceptable polymorph may be a crystalline salt. In various embodiments, it is a crystalline HCl or HBr salt of the compound of Formula I. In one embodiment, it is a crystalline HCl salt with X-ray powder diffraction peaks at 9.2 (±0.4) degrees, 17.5 (±0.4) degrees, 24.5 (±0.4) degrees, 27.4 ((±0.4) degrees, and 28.2 (±0.4) degrees two theta. In another embodiment, is a crystalline HBr salt with X-ray powder diffraction peaks at 18.5 (±0.4) degrees, 21.6 (±0.4) degrees, 22.8 (±0.4) degrees, and 26.1 (±0.4) degrees two theta.

In one embodiment, the invention is directed to a method of making a pharmaceutically-acceptable polymorph of the compound of Formula I:

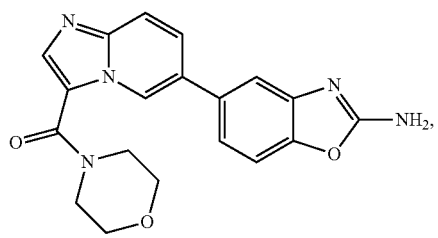 [SMILES: Nc1nc2cc(-c3ccc4ncc(C(=O)N5CCOCC5)n4c3)ccc2o1]

said method comprises (i) dissolving the compound of Formula I in an aqueous acid to result in a solution; (ii) mixing said solution with an organic solvent; and (iv) isolating said salt. In various embodiments, the organic solvent may include methanol, ethanol, THF, nitromethane, acetonitrile, methylethyl ketone (MEK), ethyl acetate, 1,4-dioxane, dichloromethane, DMSO, methyl t-butyl ether (TBME), isopropyl alcohol (IPA), acetone, N-methyl pyrrolidone (NMP), butyl acetate, or toluene. In one embodiment, the organic solvent is THF. In various embodiments, the acid may include naphthalene sulfonic acid, naphthalene disulfonic acid, L-aspartic acid, p-toluenesulfonic acid, ethane-1,2-disulfonic acid (EDSA), hydrochloric acid (HCl), hydrobromic acid (HBr), citric acid, 2-hydroxyethanesulfonic acid, fumaric acid, sulfuric acid, maleic acid, methanesulfonic acid (MSA), phosphoric acid, or oxalic acid. In one embodiment, the acid is hydrochloric acid (HCl) or hydrobromic acid (HBr). In various embodiments, the concentration of aqueous HCl may be from 1% to 37% by weight. In a further embodiment, the concentration of aqueous HCl is 36-37% by weight. In various embodiments, the concentration of aqueous HBr may be from 1%-48% by weight. In a further embodiment, the concentration of aqueous HBr is 47-48% by weight.

In various embodiments, the pharmaceutically-acceptable salt may be a crystalline salt. In one embodiment, it is a crystalline HCl or HBr salt of the compound of Formula I. In one embodiment, it is a crystalline HCl salt with X-ray powder diffraction peaks at 8.0 (±0.4) degrees, 16.0 (±0.4) degrees, 19.0 (±0.4) degrees, 26.5 (±0.4) degrees, and 27.7 (±0.4) degrees two theta. In another embodiment, is a crystalline HBr salt with X-ray powder diffraction peaks at 9.1 (±0.4) degrees, 17.3 (±0.4) degrees, 21.1 (±0.4) degrees, and 27.2 (±0.4) degrees two theta.

In one embodiment, the invention is directed to a crystalline polymorph of the HCl salt of the compound of Formula I:

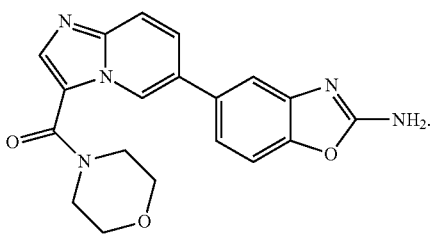 [SMILES: Nc1nc2cc(-c3ccc4ncc(C(=O)N5CCOCC5)n4c3)ccc2o1]

In one embodiment, the crystalline HCl salt has X-ray powder diffraction peaks at 9.2 (±0.4) degrees, 17.5 (±0.4) degrees, 24.5 (±0.4) degrees, 27.4 (±0.4) degrees, and 28.2 (±0.4) degrees two theta. In another embodiment, the crystalline HCl salt has X-ray powder diffraction peaks at 8.0 (±0.4) degrees, 16.0 (±0.4) degrees, 19.0 ((±0.4), 26.5 (±0.4), and 27.7 (±0.4) degrees two theta.

In one embodiment, the invention is directed to a crystalline polymorph of the HBr salt of the compound of Formula I:

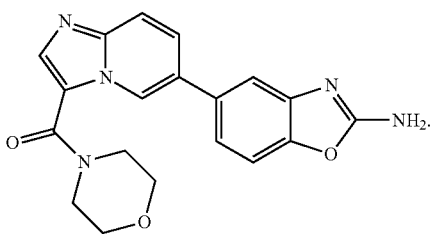 [SMILES: Nc1nc2cc(-c3ccc4ncc(C(=O)N5CCOCC5)n4c3)ccc2o1]

In one embodiment, the crystalline HBr salt has X-ray powder diffraction peaks at 18.5 (±0.4) degrees, 21.6 (±0.4) degrees, 22.8 (±0.4) degrees, and 26.1 (±0.4) degrees two theta. In another embodiment, the crystalline HBr salt has X-ray powder diffraction peaks at 9.1 (±0.4) degrees, 17.3 (±0.4) degrees, 21.1 (±0.4) degrees, and 27.2 (±0.4) degrees two theta.

In various embodiments, the invention is directed to a pharmaceutical composition comprising a therapeutically effective amount of an HCl salt of the compound of Formula I:

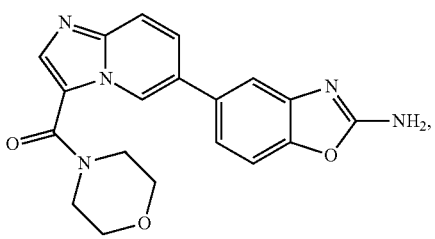 [SMILES: Nc1nc2cc(-c3ccc4ncc(C(=O)N5CCOCC5)n4c3)ccc2o1]

and a pharmaceutically acceptable carrier. In one embodiment, the therapeutically effective HCl salt has X-ray powder diffraction peaks at 9.2 (±0.4) degrees, 17.5 (±0.4) degrees, 24.5 (±0.4) degrees, 27.4 (±0.4) degrees, and 28.2 (±0.4) degrees two theta. In another embodiment, the therapeutically effective HCl salt has X-ray powder diffraction peaks at 8.0 (±0.4) degrees, 16.0 (±0.4) degrees, 19.0 (±0.4) degrees, 26.5 (±0.4) degrees, and 27.7 (±0.4) degrees two theta.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DESCRIPTION OF THE DRAWINGS

The novel features of the invention are set forth with particularity in the appended claims. An understanding of the features and advantages of the present invention may be obtained by reference to the following detailed description that sets forth illustrative embodiments, in which the principles of the invention are utilized, and the accompanying drawings of which:

DETAILED DESCRIPTION OF THE INVENTION

Figure 1:
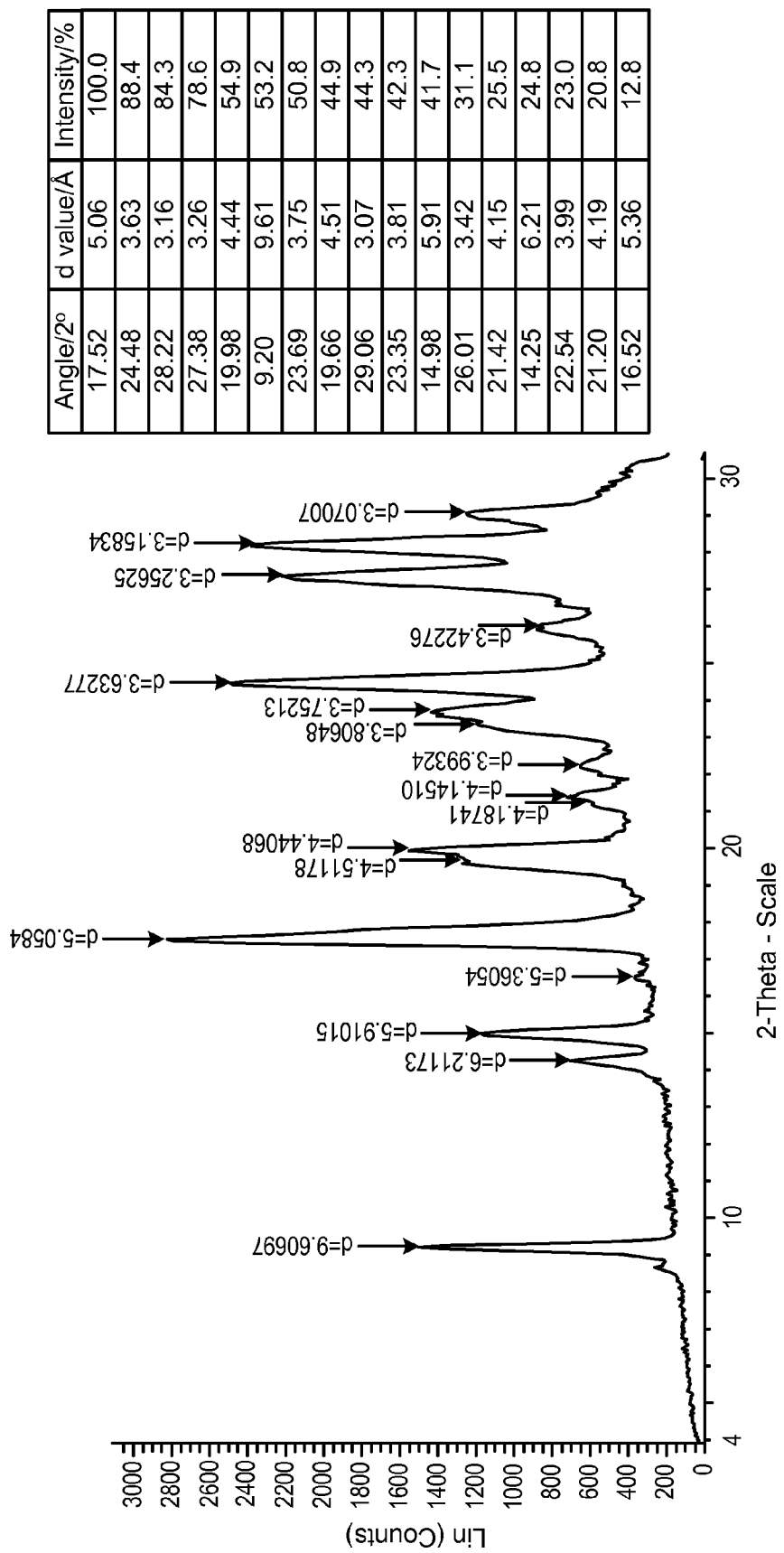
FIG. 1 shows XRPD patterns of HCl Pattern 1.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the appended claims define the scope of the invention and that methods and structures within the scope of these claims and their equivalents be covered thereby.

I. Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of the present invention.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g. bind to) the target, compounds that initiate or enhance a biological activity of the target polypeptide by interacting with other members of the signal transduction pathway of which the target polypeptide is a member are also specifically included within this definition.

The terms "antagonist" and "inhibitor" are used interchangeably, and they refer to a compound having the ability to inhibit a biological function of a target protein, whether by inhibiting the activity or expression of the target protein. Accordingly, the terms "antagonist" and "inhibitors" are defined in the context of the biological role of the target protein. While preferred antagonists herein specifically interact with (e.g. bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, the terms "treatment", "treating", "palliating" and "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, tetraalkylammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. Bis salts (i.e. two counterions), tris salts, and higher salts are encompassed within the meaning of pharmaceutically acceptable salts.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

"Subject" refers to an animal, such as a mammal, for example a human. The methods described herein can be useful in both human therapeutics and veterinary applications. In some embodiments, the patient is a mammal, and in some embodiments, the patient is human.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems,"A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

The term "in vivo" refers to an event that takes place in a subject's body.

The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass a cell-free assay in which no intact cells are employed.

The term "isolating" also encompasses purifying.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^{3}$H), iodine-125 ($^{125}$I) or carbon-14 ($^{14}$C). All isotopic variations of the compounds of the present invention, whether radioactive or not, are encompassed within the scope of the present invention.

When ranges are used herein for physical properties, such as molecular weight, or chemical properties, such as chemical formulae, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features. The phrase "consists essentially of" excludes unnamed components which materially change the material or composition in major proportions and/or in trace amounts.

The terms "solvent," "organic solvent," or "inert solvent" each mean a solvent inert under the conditions of the reaction being described in conjunction therewith including, for example, benzene, toluene, acetonitrile, tetrahydrofuran ("THF"), dimethylformamide ("DMF"), methyl t-butyl ether (MTBE), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of a limiting reagent, one cc (or mL) of solvent constitutes a volume equivalent.

"Solvate" refers to a compound (e.g., a compound as described herein or a pharmaceutically acceptable salt thereof) in physical association with one or more molecules of a pharmaceutically acceptable solvent.

"Crystalline form," "polymorph," and "form" may be used interchangeably herein, and are meant to include all crystalline and amorphous forms of the compound, including, for example, polymorphs, pseudopolymorphs, salts, solvates, hydrates, unsolvated polymorphs (including anhydrates), conformational polymorphs, and amorphous forms, as well as mixtures thereof, unless a particular crystalline or amorphous form is referred to. Compounds of the present invention include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof.

The term "HCl Pattern" refers to a particular form which is an HCl salt of a compound. Similarly, the term "HBr Pattern" refers to a particular form which is an HBr salt of a compound. As used herein, the terms "HCl Pattern 1" and "HCl Pattern 2" refer to particular forms of HCl salts of a compound of Formula I. Similarly, "HBr Pattern 1", "HBr Pattern 2", and "HBr Pattern 3" refer to particular forms of HBr salts of a compound of Formula I.

Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

II. Compounds and Methods of Making

The chemical entities described herein can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The polymorphs made according to the methods of the invention may be characterized by any methodology according to the art. For example, the polymorphs made according to the methods of the invention may be characterized by X-ray powder diffraction (XRPD), differential scanning calorimetry (DSC), thermogravimetric analysis (TGA), hot-stage microscopy, and spectroscopy (e.g., Raman, solid state nuclear magnetic resonance (ssNMR), and infrared (IR)).

XRPD

Polymorphs according to the invention may be characterized by X-ray powder diffraction patterns (XRPD). The relative intensities of XRPD peaks can vary, depending upon the sample preparation technique, the sample mounting procedure and the particular instrument employed. Moreover, instrument variation and other factors can affect the 2-θ values. Therefore, the XRPD peak assignments can vary by plus or minus about 0.1, 0.2, 0.3, or 0.4 degrees. For instance, in some embodiments the 2-θ values of a Pattern of the invention vary by plus or minus about 0.4 degrees. In other embodiments, the 2-θ values of a Pattern of the invention vary by plus or minus about 0.2 degrees. In still other embodiments, the 2-θ values of a Pattern of the invention vary by plus or minus about 0.1 degrees.

DSC

Polymorphs according to the invention can also be identified by its characteristic differential calorimeter scanning (DSC) trace such as shown in the Figures. For DSC, it is known that the temperatures observed will depend upon the rate of temperature change as well as sample preparation technique and the particular instrument employed. Thus, the values reported herein relating to DSC thermograms can vary by plus or minus about 4, 6, 8 or 10° C. For instance, the values can vary by plus or minus about 6° C.

TGA

The polymorphic forms of the invention may also give rise to thermal behavior different from that of the amorphous material or another polymorphic form. Thermal behavior may be measured in the laboratory by thermogravimetric analysis (TGA) which may be used to distinguish some polymorphic forms from others. In one aspect, the polymorph may be characterized by thermogravimetric analysis.

GVS

Polymorphs according to the invention can also be identified by gravimetric vapor sorption (GVS), which measures rate and amount of solvent absorption by a sample. In one aspect, the polymorph may be characterized by gravimetric vapor sorption analysis.

Polymorphs

The polymorph forms of the invention are useful in the production of medicinal preparations and can be obtained by means of a crystallization process to produce crystalline and semi-crystalline forms or a solidification process to obtain the amorphous form. In various embodiments, the crystallization is carried out by either generating the compound of Formula I in a reaction mixture and isolating the desired polymorph from the reaction mixture, or by dissolving raw compound in a solvent, optionally with heat, followed by crystallizing/solidifying the product by cooling (including active cooling) and/or by the addition of an antisolvent for a period of time. The crystallization or solidification may be followed by drying carried out under controlled conditions until the desired water content is reached in the end polymorphic form.

In one aspect, the invention provides methods of making one or more polymorphs of the compound of the Formula I:

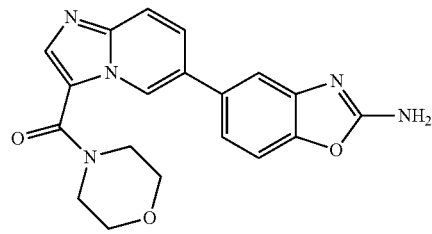 [SMILES: Nc1nc2cc(-c3ccc4ncc(C(=O)N5CCOCC5)n4c3)ccc2o1]

or a pharmaceutically acceptable salt and/or solvate thereof. Polymorphs according to the methods of the invention can be selected from HCl Pattern 1, HCl Pattern 2, HBr Pattern 1, HBr Pattern 2, HBr Pattern 3, an amorphous form, and mixtures of more than one form. In addition, polymorphs made according to the invention may include solvates. In various embodiments, polymorphs of the invention are prepared as the free base, the mono-salt, or the bis-salt, such as the HCl salt or the bis-HCl salt of the compound of Formula I, or the HBr salt of the compound of Formula I.

In various embodiments, the compound of Formula I is synthesized according to the following schemes.

Scheme 1

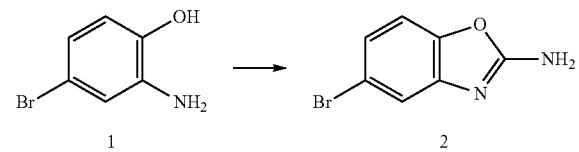

The conversion of compound 1 to compound 2 may be performed according to any method in the art. In one embodiment, compound 1 is treated with cyanogen bromide in methanol at a temperature above room temperature to yield compound 2.

Scheme 2

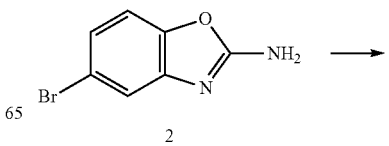

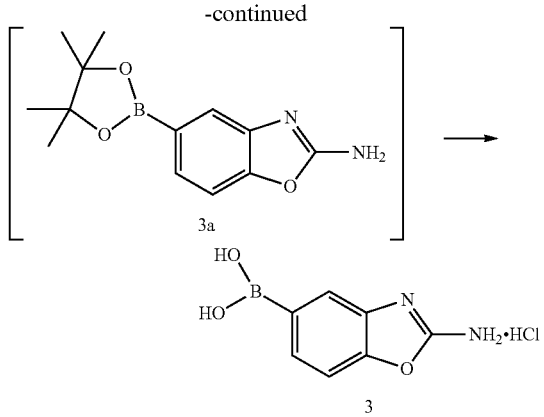

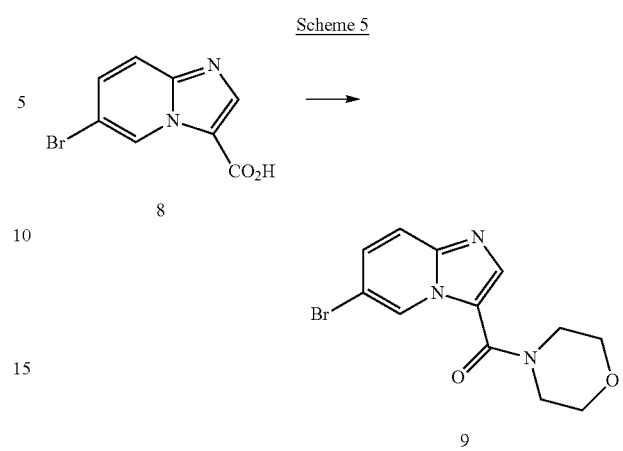

The conversion of compound 2 to compound 3 may be performed according to any method in the art. In various embodiments, compound 2 can be converted to compound 3a via a transition-metal catalyzed cross-coupling reaction with a diboron reagent. In one embodiment, compound 2 is treated with bis-(pinacolato)diboron, 1,1'-Bis[(Diphenylphosphino)ferrocene dichloropalladium (II) complexed with dichloromethane, and potassium acetate in 1,4-dioxane at an elevated temperature to give the boronic ester 3a. In one embodiment, compound 3a is further treated with acid, for example aqueous HCl, at elevated temperature to yield compound 3, the boronic acid derivative.

The conversion of compound 8 to compound 9 may be performed according to any method in the art. In one embodiment, compound 8 is first converted to its acid chloride upon treatment with thionyl chloride in 1,4-dioxane in the presence of a catalytic amount of DMF. The resulting acid chloride reacts with morpholine to yield compound 9.

Scheme 3

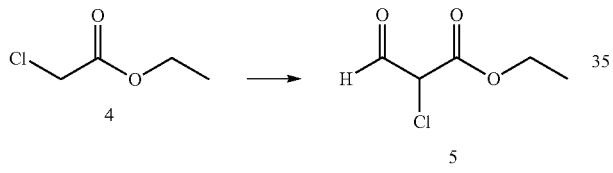

The conversion of compound 4 to compound 5 may be performed according to any method in the art. In one embodiment, the compound 4 is treated with ethyl formate and sodium ethoxide in methyl t-butyl ether to yield compound 5.

Scheme 4

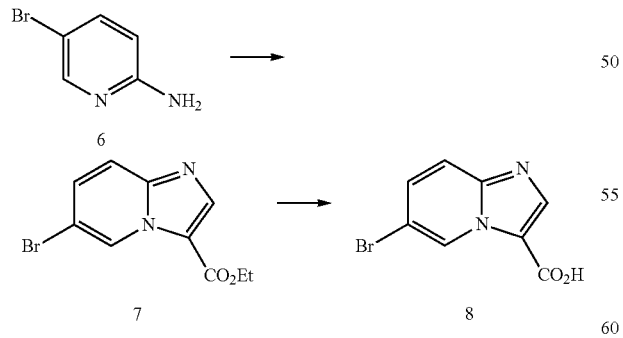

The conversion of compound 6 to compound 8 may be performed according to any method in the art. In one embodiment, compound 5 and 6 are heated to reflux in methanol to yield compound 7. Further hydrolysis of compound 7 with aqueous NaOH provides compound 8 after acidic aqueous work-up.

Scheme 6

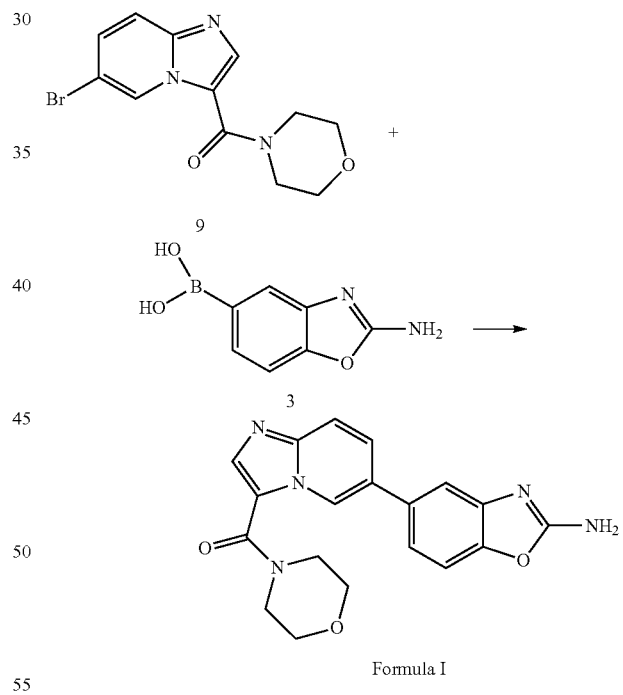

The conversion of compound 8 to compound 9 may be performed according to any method in the art. In various embodiments, compound 9 can be coupled with compound 3 to yield the compound of Formula I via a cross-coupling reaction, such as a transition-metal catalyzed coupling reaction. In one embodiment, compounds 9 and 3 are heated in 1,4-dioxane/water in the presence of Pd(PPh$_3$)$_4$ and sodium carbonate to yield the compound of Formula I. Workup of the reaction product may include treatment of a solution of the compound of Formula I with activated charcoal to remove palladium.

In one aspect, the invention is directed to methods of making polymorphs of the compound of the Formula I:

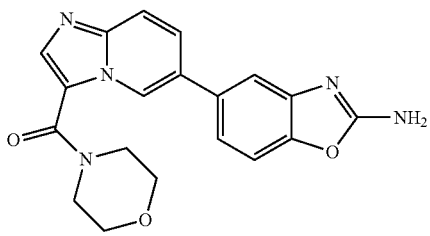 [SMILES: Nc1nc2cc(-c3ccc4ncc(C(=O)N5CCOCC5)n4c3)ccc2o1]

or a polymorph of a salt of a compound of Formula I, comprising suspending or dissolving the compound of Formula I in a solvent system, adding an acid to the suspension to result in a mixture, subjecting the mixture to a heating or cooling cycle, and isolating the polymorph. In another aspect, a polymorph of the compound of Formula I, or a polymorph of a salt of a compound of Formula I, is prepared by suspending or dissolving a compound of Formula I in an aqueous acid, adding an organic solvent system, and isolating the polymorph.

In various embodiments, the solvent system is an organic solvent system. For example, the solvent system includes methanol, ethanol, THF, nitromethane, acetonitrile, methylethyl ketone (MEK), ethyl acetate, 1,4-dioxane, dichloromethane, DMSO, methyl t-butyl ether (MTBE), isopropyl alcohol (IPA), acetone, N-methyl pyrrolidone (NMP), butyl acetate, or toluene. In various embodiments, the organic solvent system includes methanol, ethanol, THF, nitromethane, acetonitrile, methylethyl ketone (MEK), ethyl acetate, 1,4-dioxane, dichloromethane, DMSO, methyl t-butyl ether (MTBE), isopropyl alcohol (IPA), acetone, N-methyl pyrrolidone (NMP), butyl acetate, or toluene. In one embodiment, the organic solvent system is an organic solvent which is nitromethane, THF, methylethyl ketone (MEK), or acetonitrile.

In various embodiments, the polymorph is obtained by suspending or dissolving a compound of Formula I in an aqueous solvent system comprising an acid. For example, the acid is naphthalene sulfonic acid, naphthalene disulfonic acid, L-aspartic acid, p-toluenesulfonic acid, ethane-1,2-disulfonic acid (EDSA), hydrochloric acid (HCl), hydrobromic acid (HBr), citric acid, 2-hydroxyethanesulfonic acid, fumaric acid, sulfuric acid, maleic acid, methanesulfonic acid (MSA), phosphoric acid, or oxalic acid. For example, the compound of Formula I is suspended or dissolved in aqueous hydrochloric or hydrobromic acid, resulting in a slurry or solution. Mixing or stirring may be performed. The concentration of aqueous hydrochloric acid may be, for example, between 1% and 37% by weight. In some embodiments, the concentration of hydrochloric acid is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36% or 37% by weight. For example, 35-37% hydrochloric acid by weight is used. In other embodiments, aqueous hydrobromic acid is used and the concentration of aqueous hydrobromic acid is, for example, between 1% and 48% by weight. In some embodiments, the concentration of hydrobromic acid is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, or 48% by weight. For example, 46-48% hydrobromic acid by weight is used.

In some embodiments, a heating or cooling cycle is used to prepare a polymorph of the invention. For example, the heating cycle starts between −5° C. and 30° C., between 0° C. and 30° C., between 10° C. and 30° C., or between 20° C. and 30° C. In some embodiments, the heating cycle starts from room temperature (between about 20 and 25° C.). The heating cycle is conducted up to a temperature of about 40, 45, 50, 55, 60, 65, 70, 75, 80, 85, 90, 95, 100° C. or above. For example, the heating cycle is conducted up to a temperature between about 40° C. and 100° C., 60° C. and 100° C., 80° C. and 100° C., or 90° C. and 100° C. The heating may be conducted at any rate, for example between 0.1 and 10° C. per minute. In some embodiments, the heating is conducted or ramped at a rate of between 0.1 and 10° C. per minute, between 0.5 and 10° C. per minute, between 1 and 10° C. per minute, between 2 and 10° C. per minute, between 5 and 10° C. per minute, between 10 and 20° C. per minute or between 10 and 30° C. per minute.

In some embodiments, a cooling cycle is used. For example, the cooling cycle starts between 15° C. and 30° C., between 30° C. and 60° C., between 40° C. and 90° C., or between 40° C. and 100° C. In some embodiments, the cooling cycle starts from room temperature (between about 20 and 25° C.). In other embodiments, the cooling cycle starts from over 100° C. In other embodiments, the cooling cycle starts at a temperature between 70 and 100° C. The cooling cycle is conducted down to a temperature of about 90, 80, 70, 60, 50, 40, 30, 25, 20, 15, 10, 5, 0° C. or below. For example, the cooling cycle is conducted down to a temperature between about 0° C. and 40° C., 0° C. and 30° C., 10° C. and 30° C., or 15° C. and 25° C. The cooling may be conducted at any rate, for example between 0.1 and 10° C. per minute. In some embodiments, the cooling is conducted or ramped at a rate of between 0.1 and 10° C. per minute, between 0.5 and 10° C. per minute, between 1 and 10° C. per minute, between 2 and 10° C. per minute, between 5 and 10° C. per minute, between 10 and 20° C. per minute or between 10 and 30° C. per minute.

Each heating or cooling cycle may be performed as long as necessary to raise the temperature to the desired level. For example, a heating cycle may last between 1 minute and 5 minutes, between 5 minute and 10 minutes, between 10 minutes and 1 hour, or between 1 hour and 24 hours. In some embodiments, a cooling cycle is used which lasts between 1 hour and 10 weeks, or between 5 hours and 1 week, or between 24 hours and 72 hours.

In one aspect, the invention is directed to methods of making polymorphs of the compound of the Formula I:

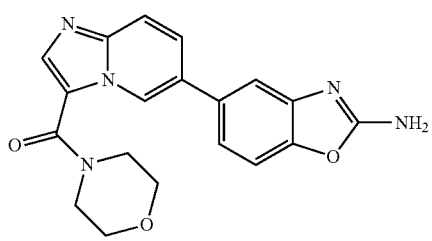 [SMILES: Nc1nc2cc(-c3ccc4ncc(C(=O)N5CCOCC5)n4c3)ccc2o1]

or a polymorph of a salt of a compound of Formula I, either by isolation of the desired polymorph as the first solid form after synthesis of the compound of Formula I, or alternatively, by isolation of the desired polymorph as a transition from a prior solid form of the compound of Formula I. Transitions from one form to another are within the scope of the invention because they can be an alternative manufacturing method for obtaining the form desired for the production of the medicinal preparations.

In various embodiments, the invention is directed to methods of making a polymorph of the compound of Formula I, wherein the method involves converting an isolated polymorph or mixture of polymorphs into a desired polymorph. In certain embodiments, the methods comprise exposing a composition comprising one or more polymorphs to conditions sufficient to convert at least about 50% of the total amount of original polymorph(s) into at least about 50% of the desired polymorph, and isolating the desired polymorph as needed.

HCl Pattern 2

Figure 2:
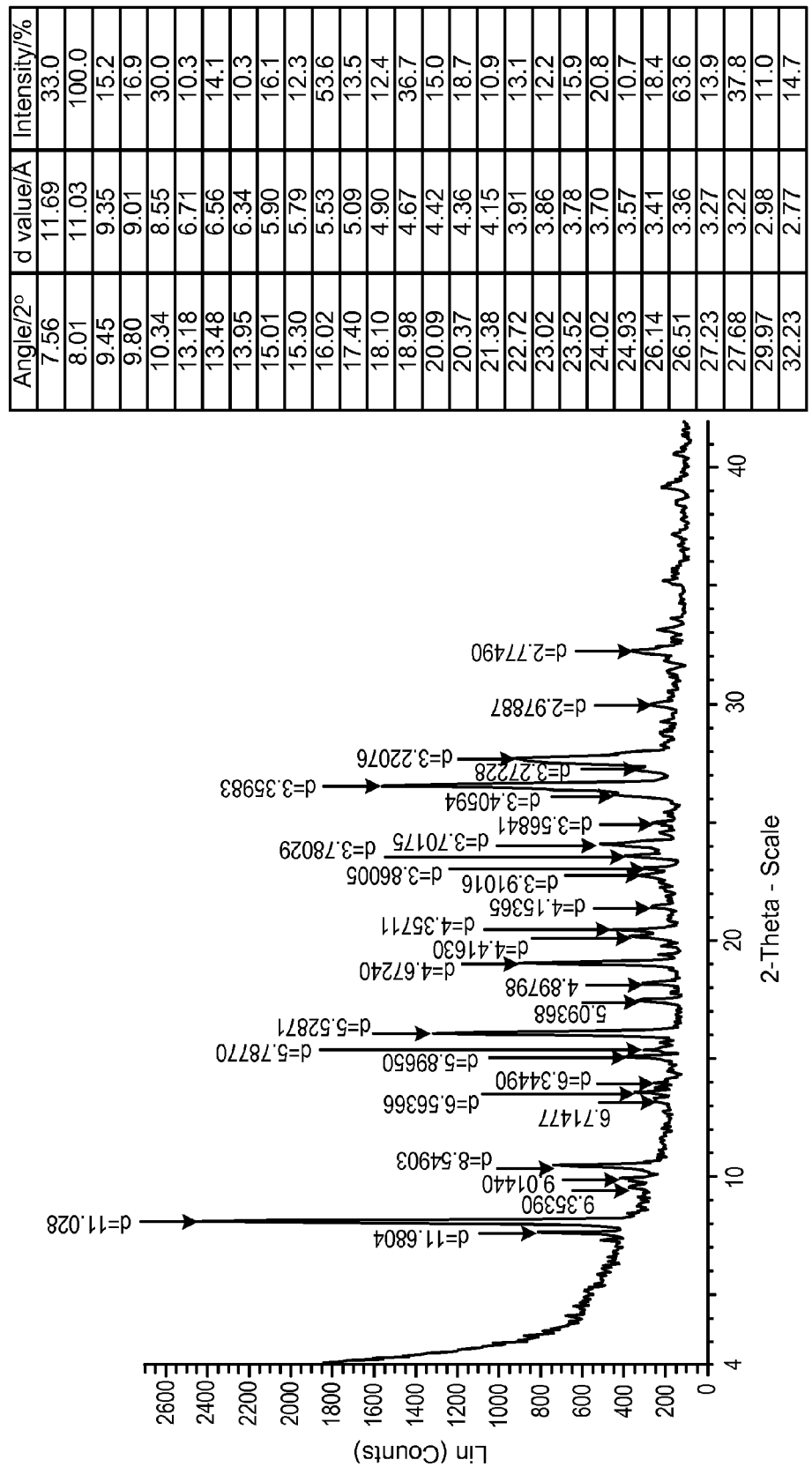
FIG. 2 shows XRPD patterns of HCl Pattern 2.
Figure 4:
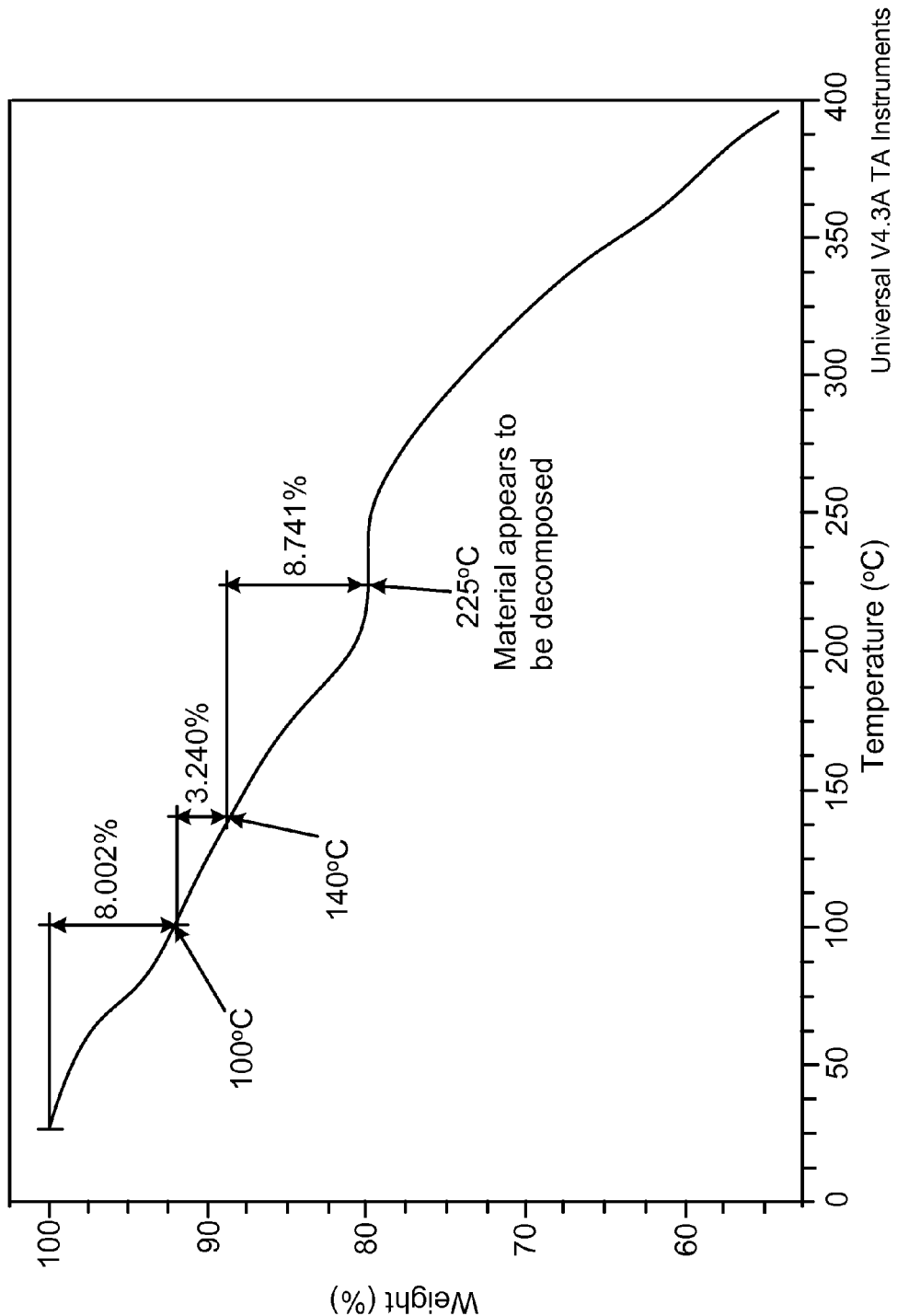
FIG. 4 shows a TGA trace of HCl Pattern 2.
Figure 5:
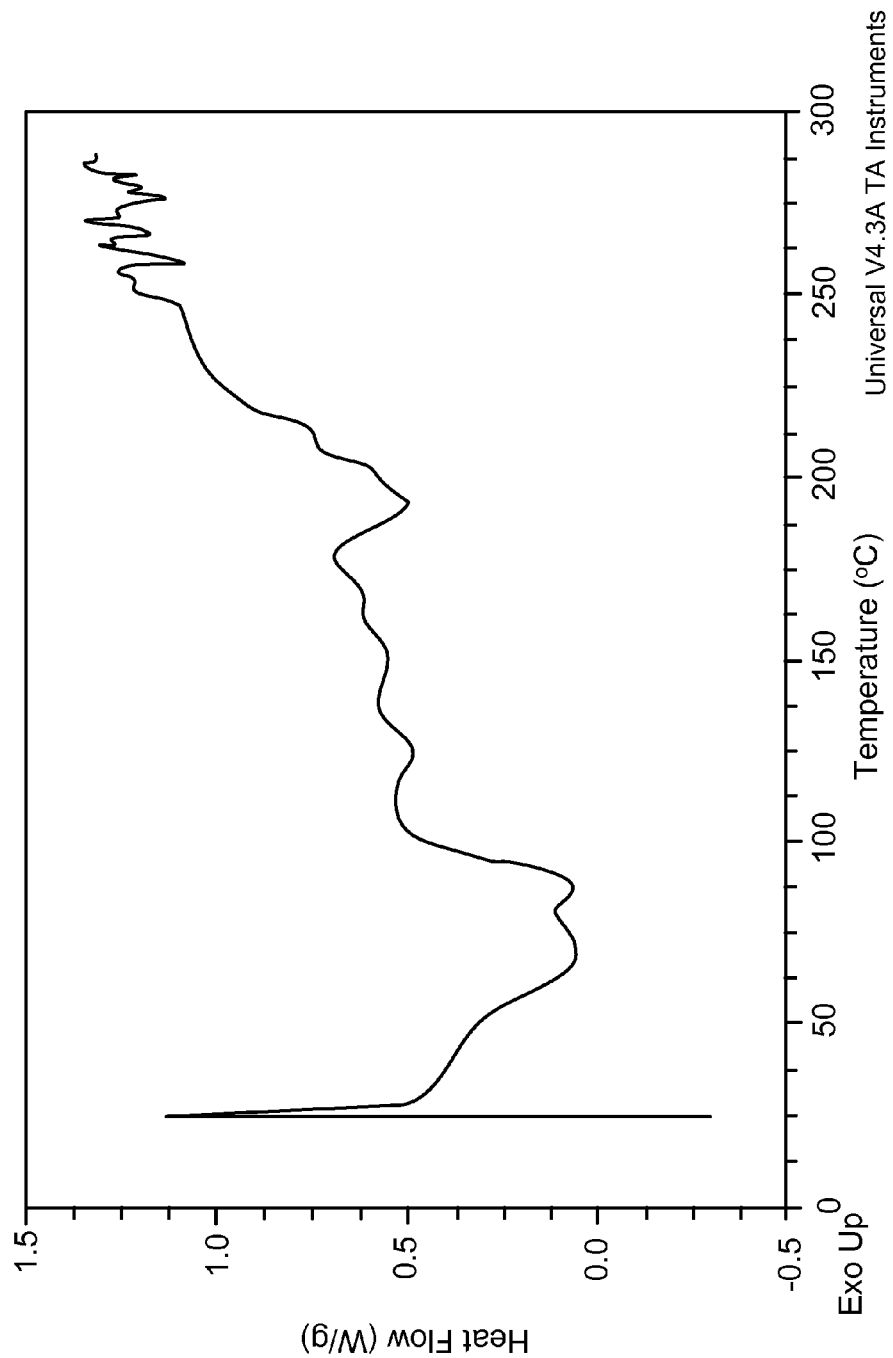
FIG. 5 shows a DSC trace of HCl Pattern 2.
Figure 6:
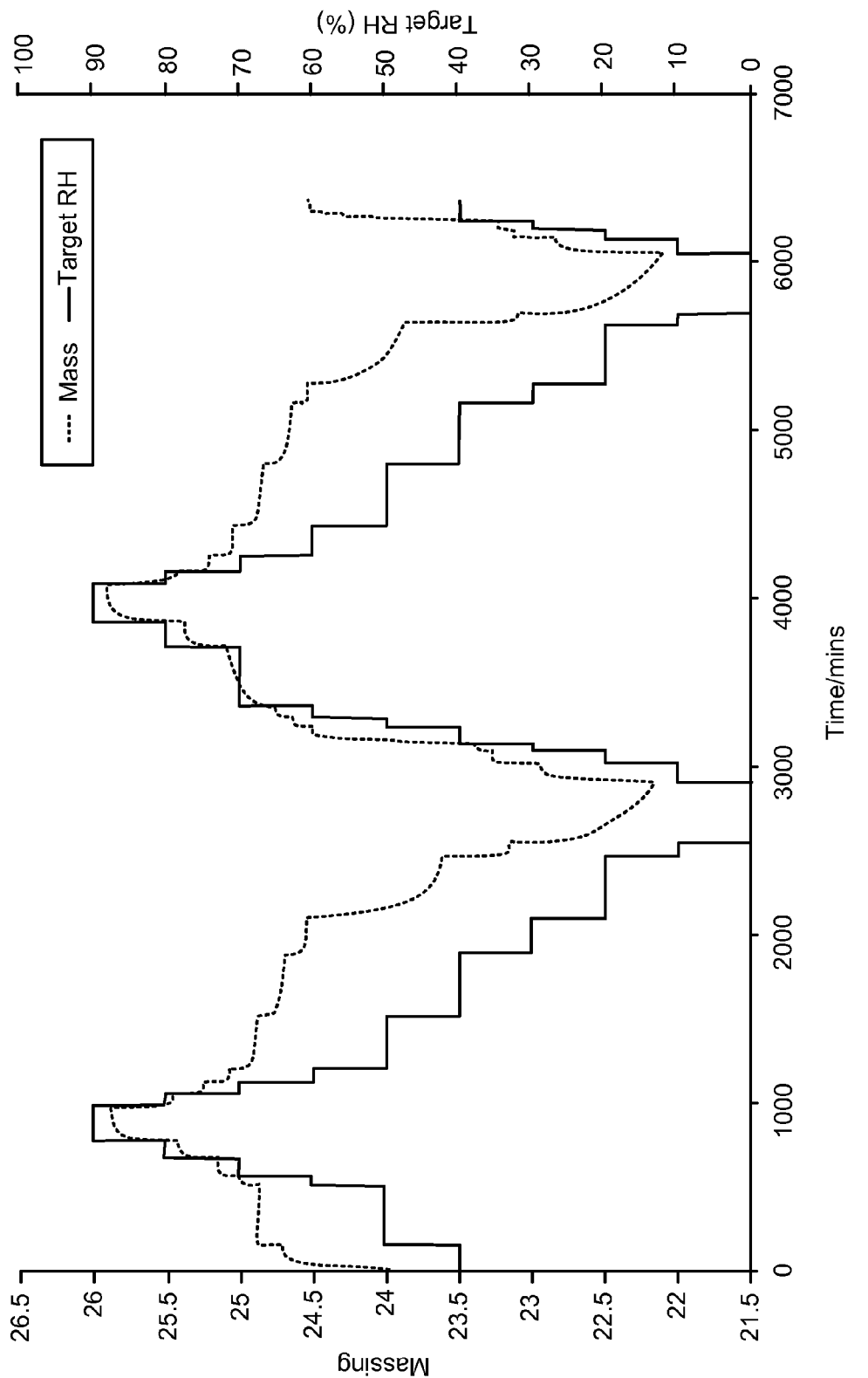
FIG. 6 shows GVS kinetic plots of HCl Pattern 2.
Figure 7:
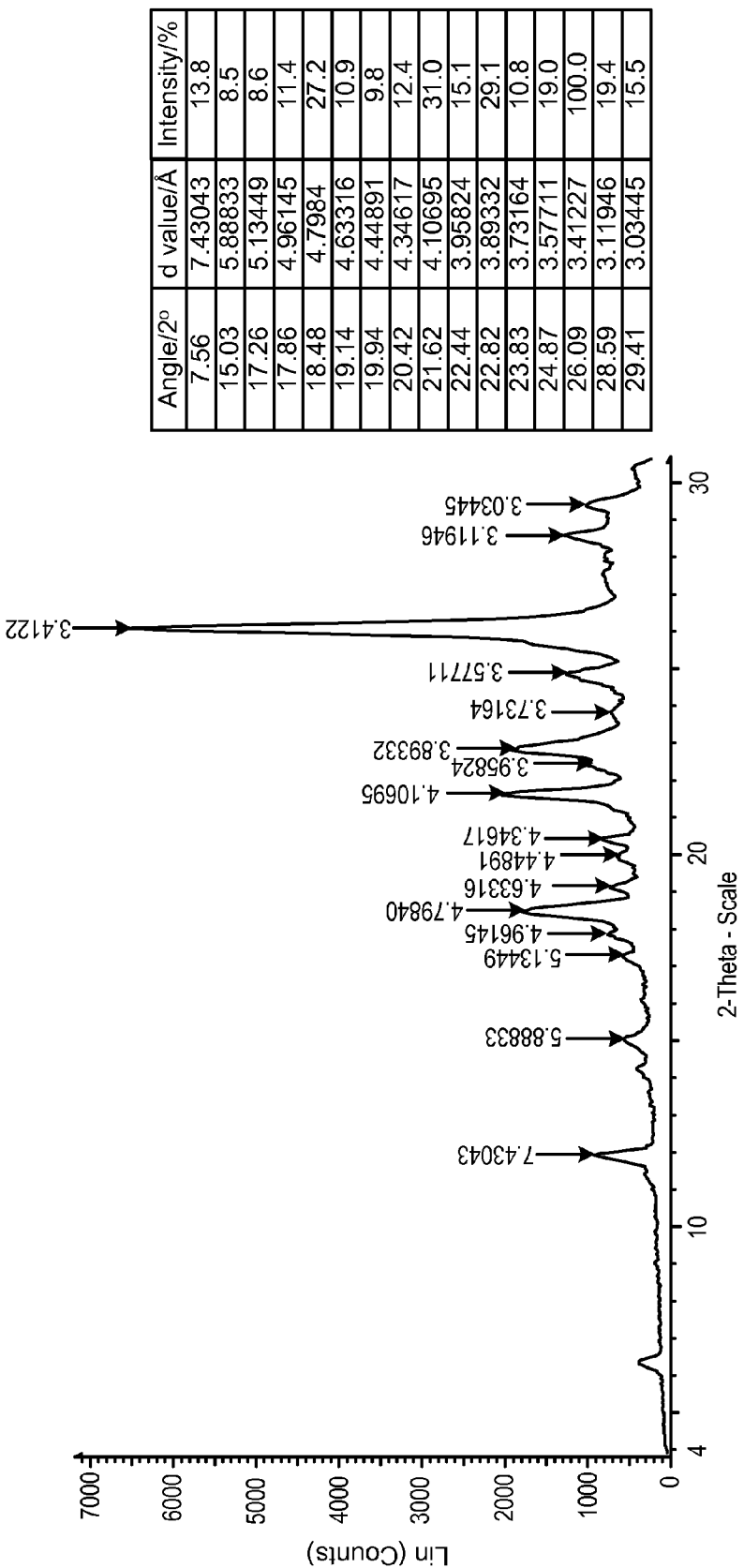
FIG. 7 shows XRPD patterns of HBr Pattern 1.
Figure 12:
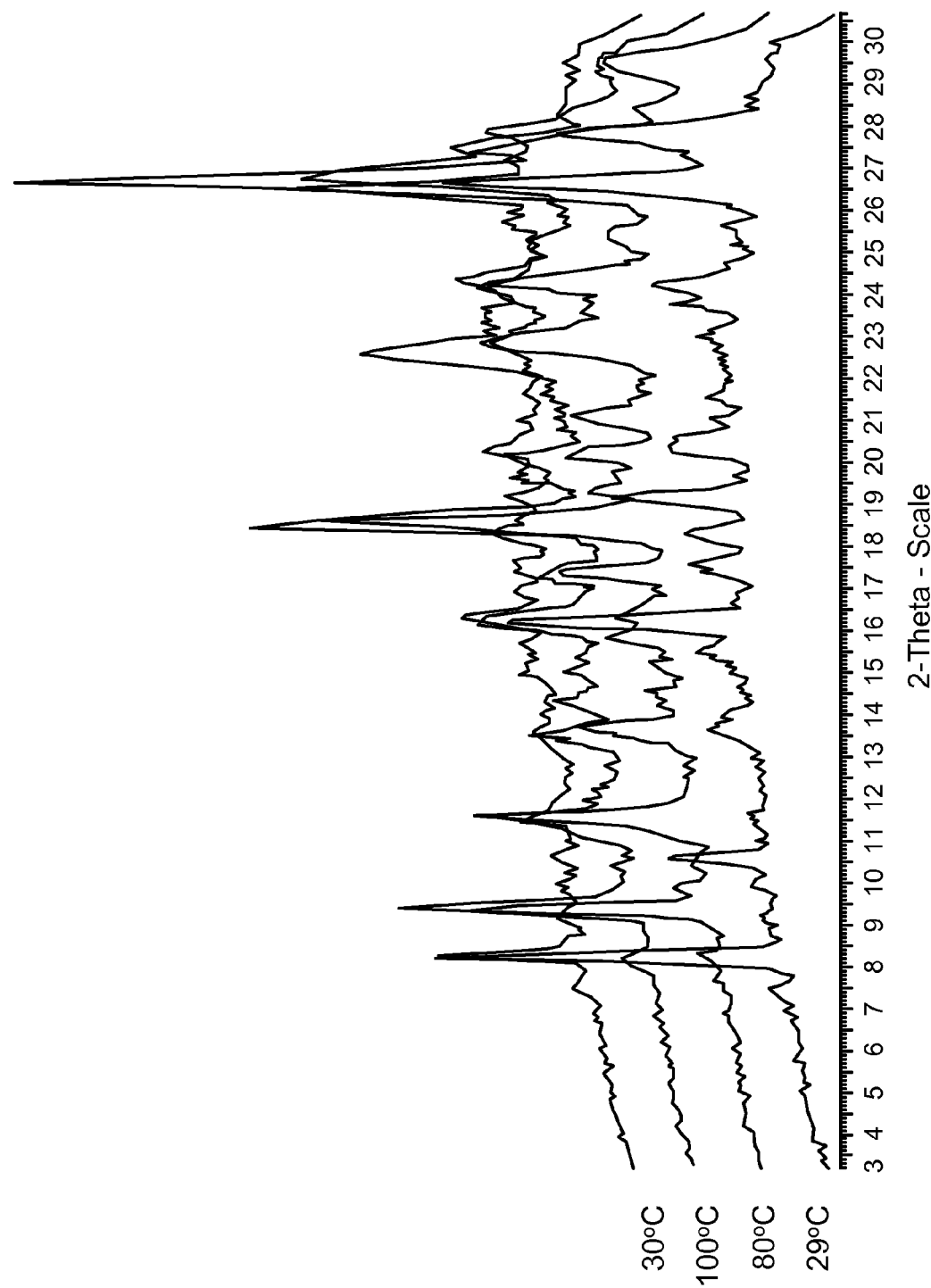
FIG. 12 shows VT-XRPD patterns of HCl Pattern 2.
Figure 13:
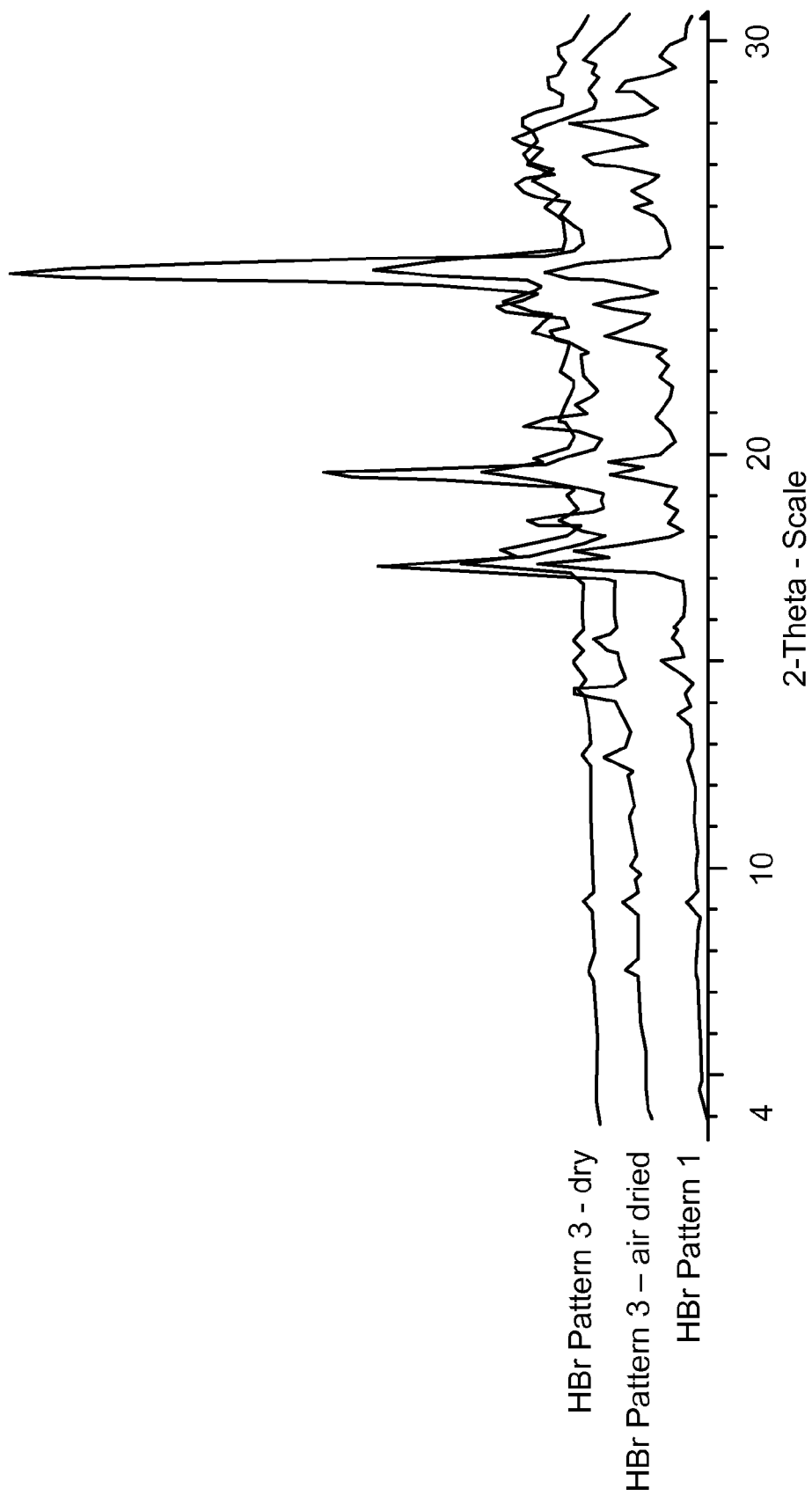
FIG. 13 shows XRPD patterns of HBr Pattern 3.
Figure 14:
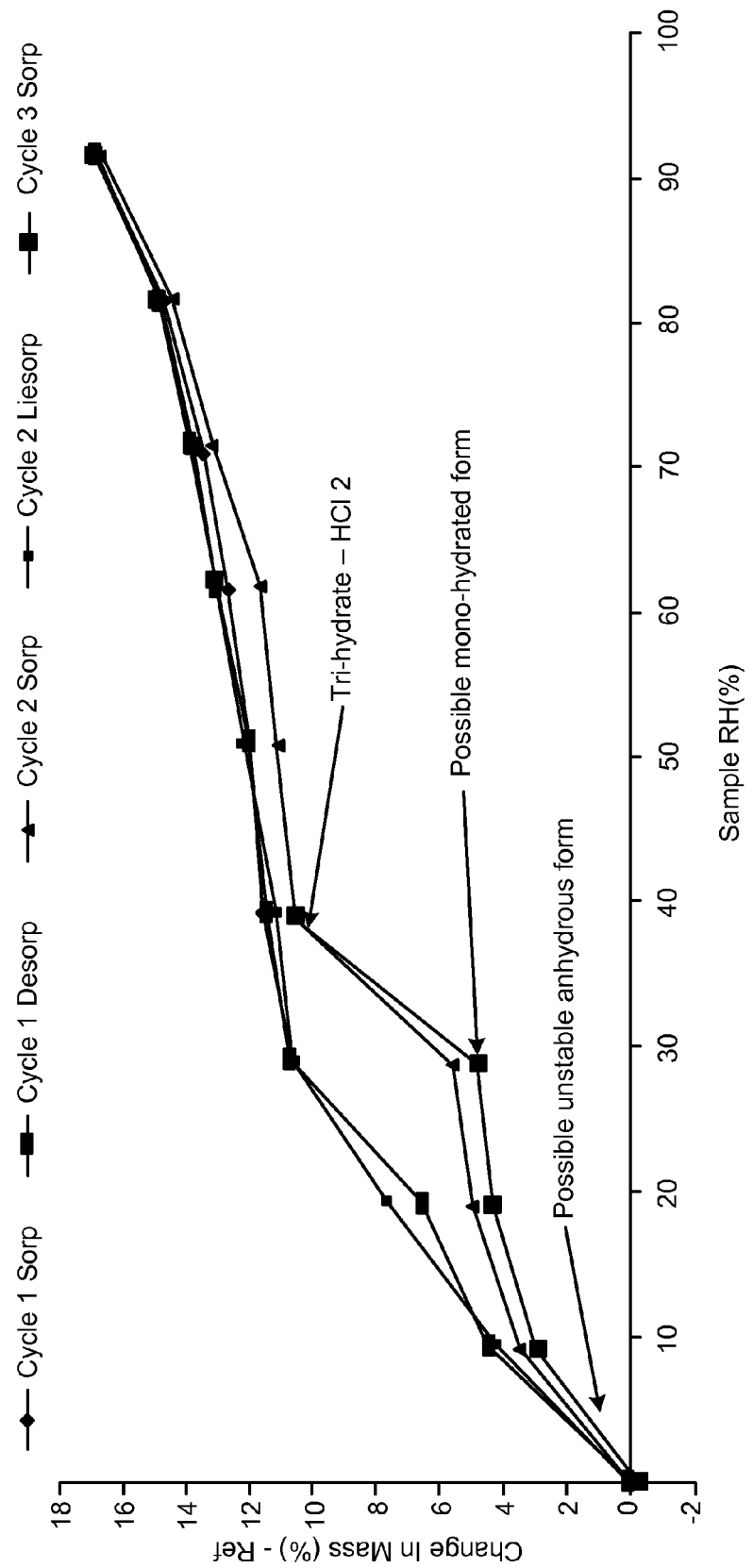
FIG. 14 shows a GVS isotherm plot of HCl Pattern 2
Figure 15:
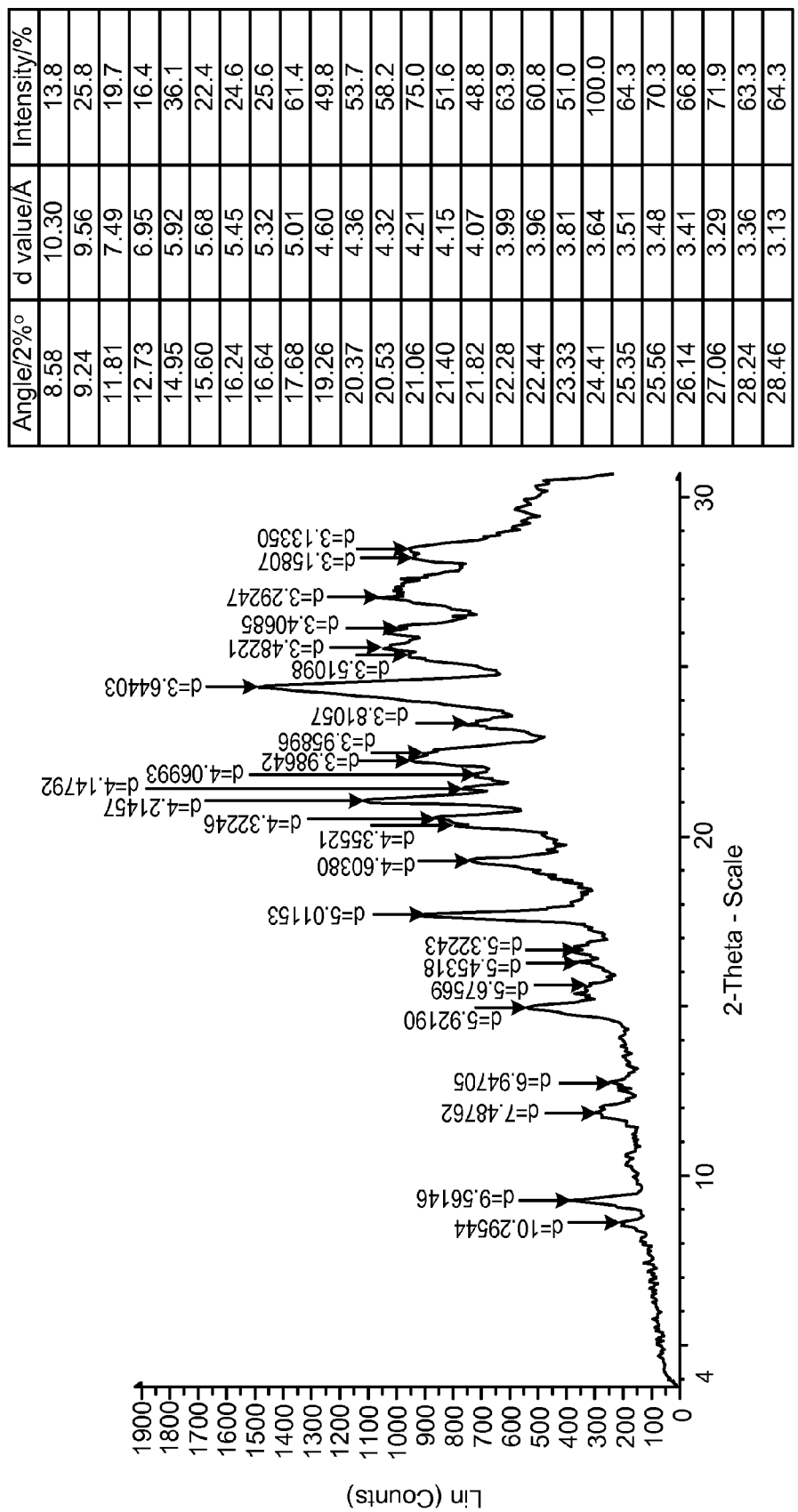
FIG. 15 shows XRPD patterns of HBr Pattern 4.

In some embodiments, the polymorph according to the invention is HCl Pattern 2. An XRPD pattern of HCl Pattern 2 is shown in FIG. 2. A TGA trace of HCl Pattern 2 is shown in FIG. 4. A DSC trace of HCl Pattern 2 is shown in FIG. 5. A GVS kinetic plot of HCl Pattern 2 is shown in FIG. 6. A VT-XRPD pattern of HCl Pattern 2 is depicted in FIG. 12. A GVS isotherm plot of HCl Pattern 2 is shown in FIG. 14.

In various embodiments, HCl Pattern 2 may be obtained in a mixture with non-HCl Pattern 2 polymorph forms. For example, in various embodiments, HCl Pattern 2 may be present as a composition further comprising one or more non-HCl Pattern 2 polymorph forms. The amount of non-HCl Pattern 2 polymorph forms may vary. For example, in various embodiments, the weight ratio of polymorph HCl Pattern 2 to the total amount of one or more non-HCl Pattern 2 polymorphs is greater than about 7:1, greater than about 8:1, greater than about 9:1, greater than about 9.5:1, or greater than about 99:1. Similarly, when formulated in pharmaceutical compositions, various amounts of non-HCl Pattern 2 polymorph forms may be present. In various embodiments the weight ratio of polymorph HCl Pattern 2 to the total amount of one or more non-HCl Pattern 2 polymorphs in a pharmaceutical composition may be greater than about 7:1, greater than about 8:1, greater than about 9:1, greater than about 9.5:1, or greater than about 99:1.

In various embodiments, HCl Pattern 2 may be produced by placing a compound of Formula I in a solvent or solvent system. For example, an organic solvent or solvent system is used. The compound of Formula I may form a suspension or slurry. Hydrochloric acid can be added to said suspension or slurry to result in a mixture. The mixture may be stirred, optionally with heating or cooling, until the desired amount of conversion to HCl Pattern 2 has occurred. In some embodiments, said mixture is subjected to at least one heating or cooling cycle without stirring.

In various embodiments, the solvent system includes methanol, ethanol, THF, nitromethane, acetonitrile, methylethyl ketone (MEK), ethyl acetate, 1,4-dioxane, dichloromethane, DMSO, methyl t-butyl ether (MTBE), isopropyl alcohol (IPA), acetone, N-methyl pyrrolidone (NMP), butyl acetate, or toluene. In various embodiments, the organic solvent system includes methanol, ethanol, THF, nitromethane, acetonitrile, methylethyl ketone (MEK), ethyl acetate, 1,4-dioxane, dichloromethane, DMSO, methyl t-butyl ether (MTBE), isopropyl alcohol (IPA), acetone, N-methyl pyrrolidone (NMP), butyl acetate, or toluene. In one embodiment, the organic solvent system is an organic solvent which is nitromethane, THF, methylethyl ketone (MEK), or acetonitrile.

In various embodiments, HCl Pattern 2 is obtained by recrystallization of a non-HCl Pattern 2 Form, including complete dissolution of the non-HCl Pattern 2 Form followed by filtration to remove any insoluble particles, and subsequent crystallization to yield HCl Pattern 2. In various embodiments, complete dissolution and filtration is not performed, in which case a slurry is formed which converts to HCl Pattern 2 without complete dissolution of one or more non-HCl Pattern 2 Forms.

In various embodiments, HCl Pattern 2 is obtained by suspending or dissolving a compound of Formula I in an aqueous solvent system comprising hydrochloric acid. For example, the compound of Formula I is suspended or dissolved in aqueous hydrochloric acid, resulting in a slurry or solution. Mixing or stirring may be performed, and optional heating or cooling cycles may be performed. In one embodiment, no heating or cooling is performed. An organic solvent or solvent system may further be mixed with the slurry or solution. For example, HCl Pattern 2 is isolated following addition of an organic solvent system comprising methanol, ethanol, THF, nitromethane, acetonitrile, methylethyl ketone (MEK), ethyl acetate, 1,4-dioxane, dichloromethane, DMSO, methyl t-butyl ether (MTBE), isopropyl alcohol (IPA), acetone, N-methyl pyrrolidone (NMP), butyl acetate, or toluene. For example, the organic solvent system is an organic solvent which is nitromethane, THF, methylethyl ketone (MEK), or acetonitrile.

The concentration of aqueous hydrochloric acid may be, for example, between 1% and 37% by weight. In some embodiments, the concentration of hydrochloric acid is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36% or 37% by weight. For example, 35-37% hydrochloric acid by weight is used.

In various embodiments, the original solid form of the compound of Formula I contains greater than about 50% non-(HCl Pattern 2) polymorphs, and the desired polymorph is HCl Pattern 2. The conversion to HCl Pattern 2 may be performed for a period of time sufficient to convert at least about 50% of the total amount of non-HCl Pattern 2 polymorphs into HCl Pattern 2 of the compound of Formula I, with an optional isolation of HCl Pattern 2 from any non-HCl Pattern 2 polymorphs, as needed.

Salt Forms

In various embodiments, the compound of Formula I is a pharmaceutically acceptable salt. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, benzene sulfonic acid, salicylic acid, 1,2-ethane disulfonic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. Bis salts (i.e. two counterions) and higher salts are encompassed within the meaning of pharmaceutically acceptable salts.

In various embodiments, salts of Formula I may be formed with sulfuric acid, p-toluenesulfonic acid, D-glucaronic acid, ethane-1,2-disulfonic acid (EDSA), 2-naphthalenesulfonic acid (NSA), hydrochloric acid (HCl) (mono and bis), hydrobromic acid (HBr), oxalic acid, naphthalene-1,5-disulfonic acid (NDSA), DL-mandelic acid, fumaric acid, sulfuric acid, maleic acid, methanesulfonic acid (MSA), benzenesulfonic acid (BSA), ethanesulfonic acid (ESA), L-malic acid, phosphoric acid, and aminoethanesulfonic acid (taurine).

III. Compositions

The invention provides compositions, including pharmaceutical compositions, comprising one or more polymorphs of the present invention. The invention further provides methods for preparing compositions as described in the Examples, and particularly Examples 1-6.

In various embodiments, the ratio of desired polymorph such as HCl Pattern 1, HCl Pattern 2, HBr Pattern 1, HBr Pattern 2, or HBr Pattern 3 to all other polymorphs may be greater than about 5:1, 6:1, 7:1, 8:1, 9:1, or more.

The subject pharmaceutical compositions are typically formulated to provide a therapeutically effective amount of a polymorph of the present invention as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject polymorphs and other agent(s) may be mixed into a preparation or both components may be formulated into separate preparations to use them in combination separately or at the same time.

In some embodiments, the concentration of one or more of the polymorphs provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the polymorphs of the present invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25% 4%, 3.75%, 3.50%, 3.25% 3%, 2.75%, 2.50%, 2.25% 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the polymorphs of the present invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the polymorphs of the present invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the polymorphs of the present invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the polymorphs of the present invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the polymorphs of the present invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The polymorphs according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day or per week. The exact dosage will depend upon the route of administration, the form in which the polymorphs is administered, the subject to be treated, the body weight of the subject to be treated, and the preference and experience of the attending physician.

Described below are non-limiting exemplary pharmaceutical compositions and methods for preparing the same.

Pharmaceutical compositions for oral administration. In some embodiments, the invention provides a pharmaceutical composition for oral administration containing a polymorph of the present invention, and a pharmaceutical excipient suitable for oral administration.

In some embodiments, the invention provides a solid pharmaceutical composition for oral administration containing: (i) an effective amount of a compound of the present invention; optionally (ii) an effective amount of a second agent; and (iii) one or more pharmaceutical excipients suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the polymorphs disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

In some cases, colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising polouxyl-40 hydrogenated castor oil, polyoxyl-60 hydrogenated castor oil or polyoxyl-100 hydrogenated castor oil.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropyl alcohol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water. In various embodiments, a solubilizer comprising polyglycol mono- and di-esters of 12-hydroxystearic acid and about 30% free polyethylene glycol (available as Solutol HS 15) is used as a solubilizer.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, antifoaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical compositions for injection. In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical compositions for topical (e.g., transdermal) delivery. In some embodiments, the invention provides a pharmaceutical composition for transdermal delivery containing a compound of the present invention and at least one pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical compositions for inhalation. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

In some embodiments, the invention provides a pharmaceutical composition for treating ophthalmic disorders. The composition is formulated for ocular administration and it contains an effective amount of one or more polymorphs of the present invention and a pharmaceutical excipient suitable for ocular administration. Pharmaceutical compositions of the invention suitable for ocular administration can be presented as discrete dosage forms, such as drops or sprays each containing a predetermined amount of an active ingredient in a solution, or a suspension in an aqueous or non-aqueous liquid, an oil-in-water emulsion, or a water-in-oil liquid emulsion. Eye drops may be prepared by dissolving the active ingredient in a sterile aqueous solution such as physiological saline, buffering solution, etc., or by combining powder compositions to be dissolved before use. Other vehicles may be chosen, as is known in the art, including but not limited to:

balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

Other pharmaceutical compositions. Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the polymorphs or pharmaceutical composition of the present invention can be effected by any method that enables delivery of the polymorphs to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Polymorphs can also be administered intraadiposally or intrathecally.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary. In various embodiments, the administration is once weekly.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, polymorphs of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Polymorphs of the invention may be applied to the surface of the stent by various methods such as dip/spin coating, spray coating, dip-coating, and/or brush-coating. The polymorphs may be applied in a solvent and the solvent may be allowed to evaporate, thus forming a layer of compound onto the stent.

Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, polymorphs of the invention may be covalently linked to a stent or graft. A covalent linker may be used which degrades in vivo, leading to the release of the compound of the invention. Any bio-labile linkage may be used for such a purpose, such as ester, amide or anhydride linkages. Polymorphs of the invention may additionally be administered intravascularly from a balloon used during angioplasty. Extravascular administration of the polymorphs via the pericardia or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The polymorphs of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

The invention also provides kits. The kits include a compound or polymorphs of the present invention as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another agent. In some embodiments, the compound of the present invention and the agent are provided as separate compositions in separate containers within the kit. In some embodiments, the compound of the present invention and the agent are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in some embodiments, be marketed directly to the consumer.

The polymorphs described herein can be used in combination with the agents disclosed herein or other suitable agents, depending on the condition being treated. Hence, in some embodiments the polymorphs of the invention will be co-administered with other agents as described above. When used in combination therapy, the polymorphs described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

IV. Methods of Treatment

The invention also provides methods of using the compounds or pharmaceutical compositions of the present invention to treat disease conditions, including but not limited to diseases associated with malfunctioning of mTOR or one or more types of PI3 kinase.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, the method of treating inflammatory or autoimmune diseases comprises administering to a subject (e.g. a mammal) a therapeutically effective amount of one or more compounds of the present invention that selectively inhibit PI3Kα as compared to all other types of kinases. Such selective inhibition may be advantageous for treating any of the diseases or conditions described herein. For example, selective inhibition may inhibit inflammatory responses associated with inflammatory diseases, autoimmune disease, or diseases related to an undesirable immune response including but not limited to asthma, emphysema, allergy, dermatitis, rhuematoid arthritis, psoriasis, lupus erythematosus, or graft versus host disease. Selective inhibition of mTOR may further provide for a reduction in the inflammatory or undesirable immune response without a concomitant reduction in the ability to reduce a bacterial, viral, and/or fungal infection.

In one aspect, one of more of the subject methods are effective in ameliorating symptoms associated with rhuematoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the pharmaceutical compositions described herein are used for the treatment of asthma. Also, the pharmaceutical compositions described herein may be used for the treatment of endotoxemia and sepsis. In one embodiment, the compositions or pharmaceutical compositions described herein are used to for the treatment of rheumatoid arthritis (RA). In yet another embodiment, the compositions or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating a hyperproliferative disorder in a mammal that comprises administering to said mammal a therapeutically effective amount of a composition of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e. g., psoriasis), restenosis, or prostate (e. g., benign prostatic hypertrophy (BPH)).

The invention also relates to a method of treating diseases related to vasculogenesis or angiogenesis in a mammal that comprises administering to said mammal a therapeutically effective amount of a composition of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compositions of the present invention, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

Patients that can be treated with compounds of the present invention, according to the methods of this invention include, for example, patients that have been diagnosed as having conditions including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphocytic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATL), cutaneous T-cell lymphoma (CTCL), large granular lymphocytic leukemia (LGF), Hodgkin's disease and Reed-Stemberg disease; acute myelocytic leukemia (AML), chronic myelocytic leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DL-BCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic andenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenstrom's macroglobulinemia.

The invention also relates to a method of treating diabetes in a mammal that comprises administering to said mammal a therapeutically effective amount of a composition of the present invention.

In addition, the compositions described herein may be used to treat acne.

In addition, the compositions described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compositions described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compositions described herein may be used for the treatment of bursitis, lupus, acute disseminated encephalomyelitis (ADEM), Addison's disease, antiphospholipid antibody syndrome (APS), aplastic anemia, autoimmune hepatitis, coeliac disease, Crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

Further, the compositions of the invention may be used for the treatment of perennial allergic rhinitis, Mesenteritis, Peritonitis, Acrodermatitis, Angiodermatitis, Atopic dermatitis, Contact dermatitis, Eczema, Erythema multiforme, Intertrigo, Stevens Johnson syndrome, Toxic epidermal necrolysis, Skin allergy, Severe allergic reaction/anaphylaxis, Allergic granulomatosis, Wegener granulomatosis, Allergic conjunctivitis, Chorioretinitis, Conjunctivitis, Infectious keratoconjunctivitis, Keratoconjunctivitis, Ophthalmia neonatorum, Trachoma, Uveitis, Ocular inflammation, Blepharoconjunctivitis, Mastitis, Gingivitis, Pericoronitis, Pharyngitis, Rhinopharyngitis, Sialadenitis, Musculoskeletal system inflammation, Adult onset Stills disease, Behcets disease, Bursitis, Chondrocalcinosis, Dactylitis, Felty syndrome, Gout, Infectious arthritis, Lyme disease, Inflammatory osteoarthritis, Periarthritis, Reiter syndrome, Ross River virus infection, Acute Respiratory, Distress Syndrome, Acute bronchitis, Acute sinusitis, Allergic rhinitis, Asthma, Severe refractory asthma, Pharyngitis, Pleurisy, Rhinopharyngitis, Seasonal allergic rhinitis, Sinusitis, Status asthmaticus, Tracheobronchitis, Rhinitis, Serositis, Meningitis, Neuromyelitis optica, Poliovirus infection, Alport syndrome, Balanitis, Epididymitis, Epididymo orchitis, Focal segmental, Glomerulosclerosis, Glomerulonephritis, IgA Nephropathy (Berger's Disease), Orchitis, Parametritis, Pelvic inflammatory disease, Prostatitis, Pyelitis, Pyelocystitis, Pyelonephritis, Wegener granulomatosis, Hyperuricemia, Aortitis, Arteritis, Chylopericarditis, Dressler syndrome, Endarteritis, Endocarditis, Extracranial temporal arteritis, HIV associated arteritis, Intracranial temporal arteritis, Kawasaki disease, Lymphangiophlebitis, Mondor disease, Periarteritis, or Pericarditis.

In other aspects, the compositions of the invention are used for the treatment of Autoimmune hepatitis, Jejunitis, Mesenteritis, Mucositis, Non alcoholic steatohepatitis, Non viral hepatitis, Autoimmune pancreatitis, Perihepatitis, Peritonitis, Pouchitis, Proctitis, Pseudomembranous colitis, Rectosigmoiditis, Salpingoperitonitis, Sigmoiditis, Steatohepatitis, Ulcerative colitis, Churg Strauss syndrome, Ulcerative proctitis, Irritable bowel syndrome, Gastrointestinal inflammation, Acute enterocolitis, Anusitis, Balser necrosis, Cholecystitis, Colitis, Crohns disease, Diverticulitis, Enteritis, Enterocolitis, Enterohepatitis, Eosinophilic esophagitis, Esophagitis, Gastritis, Hemorrhagic enteritis, Hepatitis, Hepatitis virus infection, Hepatocholangitis, Hypertrophic gastritis, Ileitis, Ileocecitis, Sarcoidosis, Inflammatory bowel disease, Ankylosing spondylitis, Rheumatoid arthritis, Juvenile rheumatoid arthritis, Psoriasis, Psoriatic arthritis, Lupus (cutaneous/systemic/nephritis), AIDS, Agammaglobulinemia, AIDS related complex, Brutons disease, Chediak Higashi syndrome, Common variable immunodeficiency, DiGeorge syndrome, Dysgammaglobulinemia, Immunoglobulindeficiency, Job syndrome, Nezelof syndrome, Phagocyte bactericidal disorder, Wiskott Aldrich syndrome, Asplenia, Elephantiasis, Hypersplenism, Kawasaki disease, Lymphadenopathy, Lymphedema, Lymphocele, Nonne Milroy Meige syndrome, Spleen disease, Splenomegaly, Thymoma, Thymus disease, Perivasculitis, Phlebitis, Pleuropericarditis, Polyarteritis nodosa, Vasculitis, Takayasus arteritis, Temporal arteritis, Thromboangiitis, Thromboangiitis obliterans, Thromboendocarditis, Thrombophlebitis, or COPD.

The invention also relates to a method of treating a cardiovascular disease in a mammal that comprises administering to said mammal a therapeutically effective amount of a composition of the present invention. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a composition of the invention.

In another aspect of the present invention, methods are provided for treating ophthalmic disease by administering one or more of the subject compositions or pharmaceutical compositions to the eye of a subject.

Methods are further provided for administering the compositions of the present invention via eye drop, intraocular injection, intravitreal injection, topically, or through the use of a drug eluting device, microcapsule, implant, or microfluidic device. In some cases, the compositions of the present invention are administered with a carrier or excipient that increases the intraocular penetrance of the composition such as an oil and water emulsion with colloid particles having an oily core surrounded by an interfacial film.

The invention further provides methods of modulating kinase activity by contacting a kinase with an amount of a composition of the invention sufficient to modulate the activity of the kinase. Modulate can be inhibiting or activating kinase activity. In some embodiments, the invention provides methods of inhibiting kinase activity by contacting a kinase with an amount of a composition of the invention sufficient to inhibit the activity of the kinase. In some embodiments, the invention provides methods of inhibiting kinase activity in a solution by contacting said solution with an amount of a composition of the invention sufficient to inhibit the activity of the kinase in said solution. In some embodiments, the invention provides methods of inhibiting kinase activity in a cell by contacting said cell with an amount of a composition of the invention sufficient to inhibit the activity of the kinase in said cell. In some embodiments, the invention provides methods of inhibiting kinase activity in a tissue by contacting said tissue with an amount of a composition of the invention sufficient to inhibit the activity of the kinase in said tissue. In some embodiments, the invention provides methods of inhibiting kinase activity in an organism by contacting said organism with an amount of a composition of the invention sufficient to inhibit the activity of the kinase in said organism. In some embodiments, the invention provides methods of inhibiting kinase activity in an animal by contacting said animal with an amount of a composition of the invention sufficient to inhibit the activity of the kinase in said animal. In some embodiments, the invention provides methods of inhibiting kinase activity in a mammal by contacting said mammal with an amount of a composition of the invention sufficient to inhibit the activity of the kinase in said mammal. In some embodiments, the invention provides methods of inhibiting kinase activity in a human by contacting said human with an amount of a composition of the invention sufficient to inhibit the activity of the kinase in said human. In some embodiments, the % of kinase activity after contacting a kinase with a composition of the invention is less than 1, 5, 10, 20, 30, 40, 50, 60, 70, 80 90, 95, or 99% of the kinase activity in the absence of said contacting step.

In some embodiments, one or more compositions of the invention selectively inhibits PI3Kα activity with an $IC_{50}$ value of about 100 nM, 50 nM, 10 nM, 5 nM, 100 pM, 10 pM or even 1 pM, or less as ascertained in an in vitro kinase assay.

V. Combination Treatment

The present invention also provides methods for combination therapies in which an agent known to modulate other pathways, or other components of the same pathway, or even overlapping sets of target enzymes are used in combination with a composition of the present invention. In one aspect, such therapy includes but is not limited to the combination of the subject composition with chemotherapeutic agents, therapeutic antibodies, and radiation treatment, to provide a synergistic or additive therapeutic effect.

In one aspect, the compositions or pharmaceutical compositions of the present invention may present synergistic or additive efficacy when administered in combination with agents that inhibit IgE production or activity. Such combination can reduce the undesired effect of high level of IgE associated with the use of one or more inhibitors, if such effect occurs. This may be particularly useful in treatment of autoimmune and inflammatory disorders (AIID) such as rheumatoid arthritis. Additionally, the administration of inhibitors of the present invention in combination with inhibitors of PI3Kα, PI3Kδ, PI3Kδ/γ, or mTor may also exhibit synergy through enhanced inhibition of the PI3K pathway.

Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compositions that inhibit mTORC1 and mTORC2. Agents that inhibit IgE activity include, for example, anti-IgE antibodies such as for example Omalizumab and TNX-901.

For treatment of autoimmune diseases, the subject compositions or pharmaceutical compositions can be used in combination with commonly prescribed drugs including but not limited to Enbrel®, Remicade®, Humira®, Avonex®, and Rebif®. For treatment of respiratory diseaseses, the subject compositions or pharmaceutical compositions can be administered in combination with commonly prescribed drugs including but not limited to Xolair®, Advair®, Singulair®, and Spiriva®.

The compositions of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin. Other compounds used in the treatment of lupus include belimumab (Benlysta®).

In another one aspect, this invention also relates to a pharmaceutical composition for inhibiting abnormal cell growth in a mammal which comprises an amount of a composition of the present invention, in combination with an amount of an anti-cancer agent (e.g. a biotherapeutic chemotherapeutic agent). Many chemotherapeutics are presently known in the art and can be used in combination with the compositions of the invention. Other cancer therapies can also be used in combination with the compositions of the invention and include, but are not limited to, surgery and surgical treatments, and radiation therapy.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Casodex (bicalutamide), Iressa (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.®.; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda;

ibandronate; camptothecin-11 (CPT-11); topoisomerase inhibitor RFS 2000; difluoromethylornithine (DMFO). Where desired, the compositions or pharmaceutical composition of the present invention can be used in combination with commonly prescribed anti-cancer drugs such as Herceptin®, AvastinO, Erbitux®, Rituxan®, Taxol®, Arimidex®, Taxotere®, and Velcade®.

Other chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulfonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab)).

This invention further relates to a method for using the compositions or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the composition of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as 1-125, 1-131, Yb-169, Ir-192 as a solid source, 1-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compositions of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a composition of the present invention, which amount is effective is sensitizing abnormal cells to treatment with radiation. The amount of the composition in this method can be determined according to the means for ascertaining effective amounts of such compositions described herein.

The compositions or pharmaceutical compositions of the present invention can be used in combination with an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a composition of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

The compositions describe herein may be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which may be administered in conjunction with the compositions described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulfonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, (3-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, beta-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject composition include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject composition may be found in Goodman and Gilman's *The Pharmacological Basis of Therapeutics*, Tenth Edition, edited by Hardman, Limbird and Gilman, or the *Physician's Desk Reference*, both of which are incorporated herein by reference in their entirety.

The compositions described herein can be used in combination with the agents disclosed herein or other suitable agents, depending on the condition being treated. Hence, in some embodiments the compositions of the invention will be co-administer with other agents as described above. When used in combination therapy, the compositions described herein may be administered with the second agent simultaneously or separately. This administration in combination can include simultaneous administration of the two agents in the same dosage form, simultaneous administration in separate dosage forms, and separate administration. That is, a composition described herein and any of the agents described above can be formulated together in the same dosage form and administered simultaneously. Alternatively, a composition of the present invention and any of the agents described above can be simultaneously administered, wherein both the agents are present in separate formulations. In another alternative, a composition of the present invention can be administered just followed by and any of the agents described above, or vice versa. In the separate administration protocol, a composition of the present invention and any of the agents described above may be administered a few minutes apart, or a few hours apart, or a few days apart.

EXAMPLES

The examples and preparations provided below further illustrate and exemplify the compositions of the present invention and methods of preparing such compositions. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

Example 1

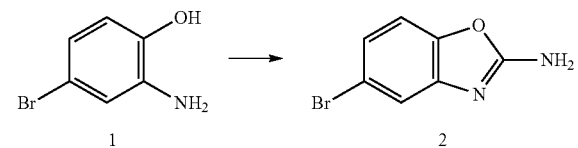 [SMILES: Nc1cc(Br)ccc1O ; Nc1nc2cc(Br)ccc2o1]

Preparation of Compound 2:

1. 2-Amino-4-bromophenol (12574 g) and methanol (100.6 L, 79.6 kg) were charged to an appropriately sized reactor and stirred at room temperature (~18 to 20° C.).

2. A solution of cyanogen bromide (8500 g) was prepared in methanol (25.1 L, 19.9 kg) in a separate 50 gallon reactor; this solution was charged to the starting material reaction mixture via an additional funnel (total reaction volume ~150 L, 40 gal).

3. The reaction mixture was heated for ~15 hours at 37° C.

4. The reaction was monitored by HPLC until it was complete.

5. Upon completion, the reaction mixture was cooled to 18-20° C.

6. 40% Sodium carbonate solution (12.41 Kg of $Na_2CO_3$ in 30.2 L water) was added at ambient temperature and the mixture was stirred for ~1 hour.

7. Solvent was distilled under vacuum at 30-40° C. to remove most of the methanol.

8. Water (50.2 L, 50.2 kg) was charged.

9. Ethyl acetate (125 L, 113 kg) was added and the resulting mixture was stirred for ~10 minutes.

10. The agitation was stopped and the layers were allowed to separate.

11. The lower aqueous phase was drained.

12. Water (50 L, 50 kg) was added to the organic layer in the reactor and the resulting mixture was stirred for at least 20 minutes.

13. The agitation was stopped and the layers were allowed to separate.

14. The lower aqueous phase was drained and combined with the aqueous phase from step 11.

15. Brine (7.0 Kg of NaCl in 25 kg of H$_2$O) was added and the resulting mixture was stirred for ~10 minutes.

16. The agitation was stopped and the layers were allowed to separate.

17. The lower aqueous phase was drained and combined with the aqueous phases from step 14.

18. Magnesium sulfate (1.9 Kg) was added and the resulting mixture was stirred for at least 15 minutes.

19. The mixture was filtered into a cleaned reactor using 1 um in-line filter.

20. The reactor and filter lines were washed with ethyl acetate (12 L).

21. Distillation was carried out under vacuum at 30-40° C. to minimum steerable volume (~2 volumes, ~25 L).

22. Heptane (63 L, 43 kg) was added.

23. Distillation was carried out under vacuum at 30-40° C. to minimum stirrable volume (~2 volumes, ~25 L).

24. Steps 22 & 23 were repeated one more time. [00252]25. Heptane (32 L) was added and the resulting mixture was stirred for at least 3 hours at ambient temperature (18° C. to 20° C.).

26. The reaction was monitored by HPLC.

27. A solid was collected by vacuum filtration and washed with heptane (2×13 L, 8.9 kg).

28. The solid was dried in a vacuum oven at ~47° C. to constant weight to give brown to light brown color solid (13510 g, 95% yield; HPLC purity 97.2%; $^1$HNMR (DMSO-d 6, 300 MHz) δ 7.6 (s, 2H), 7.38-7.28 (m, 2H), 7.15-7.08 (1H)).

Example 2

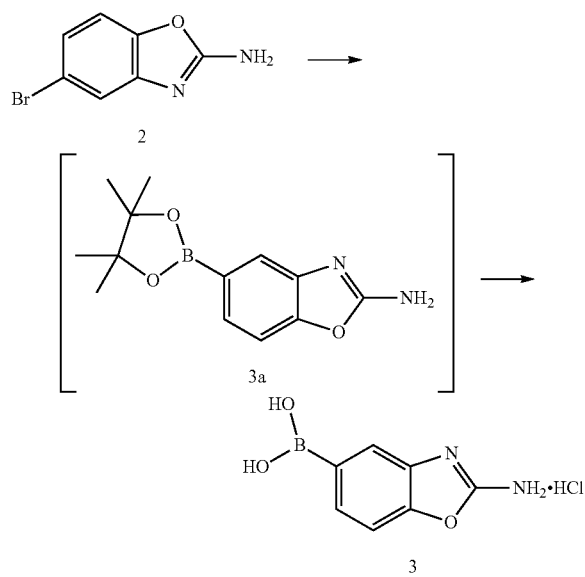

Preparation of compound 4:

1. 5-Bromobenzo[b]oxazol-2-amine (Compound 2, 13400 g), bis-(pinacolato)diboron (19168 g), and 1,4-Dioxane (134 L) were added to an appropriately sized reactor and stirred at room temperature (~18 to 20° C.).

2. With stirring, the reaction mixture was sparged with nitrogen for ~10 minutes at <20° C.

3. 1,1'-Bis[(Diphenylphosphino) ferrocene dichloropalladium (II) complexed with dichloromethane ((PdCl$_2$(dppf)$_2$), 2569 g)) and potassium acetate (KOAc, 18520 g) were added to the reactor.

4. With stirring, the sparging with nitrogen was continued for ~10 minutes at <20° C.

5. The reaction mixture was heated to reflux (100 to 103° C.) under slight nitrogen blanket and stirred for 3 to 5 hours.

6. The reaction was monitored by HPLC.

7. Upon completion, the reaction mixture was cooled to 18-20° C., filtered through a plug of silica gel (40.5 Kg; ~30 wt %).

8. The product was further eluted with Ethyl acetate (37 mL/g) under slight vacuum.

9. The last eluting fraction of the sample was submitted for TLC analysis.

10. The combined filtrates were concentrated under vacuum at 30-40° C. to a minimum stirrable volume (total ~1.5 to 2 volumes).

11. 50% Aq. hydrochloric acid (1:1, Conc HCl: H$_2$O, 10 mL/g, 67 L of Conc. HCl with 67 L of Water) was charged to the thick slur in the reactor and the reaction mixture was heated to 80 to 84° C. followed by stirring for 2-4 hours at 80 to 84° C.

12. The reaction was monitored by HPLC.

13. Upon completion, the reaction mixture was cooled to 18-20° C.

14. A solid was collected via vacuum filtration and washed with 10% aqueous hydrochloric acid (1:9, Conc HCl: H$_2$O) (13 L of Conc. HCl with 67 L of Water).

15. The light brown to brown solids (wet) was suspended in ethyl acetate (134 L) and stirred for ~30 minutes at 18-20° C.

16. The solids was collected via vacuum filtration and washed with ethyl acetate (67 L).

17. The solids was dried for ~1 hour under nitrogen blanket and then dried in a vacuum oven at ~50° C. to constant weight (~72 to 90 hours) with a slight nitrogen bleed to give compound 3 as a brown to light brown color solid (9479 g, 70% yield; HPLC purity 94.2%; $^1$HNMR (DMSO-d6, 300 MHz) δ 10.2-9.5 (1H), 7.85-7.71 (1H), 7.62-7.50 (1H)).

Example 3

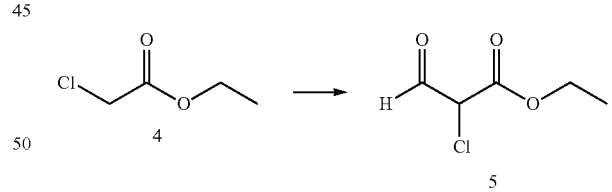

Preparation of compound 5:

1. Methyl t-butyl ether (MTBE, 102 L) was added to an appropriately sized reactor and stirred followed by the addition of sodium ethoxide (6230 g) at room temperature under nitrogen atmosphere.

2. The resulting suspension was stirred for 15 min at room temperature, then cooled to 5 to 0° C.

3. A mixture of ethylformate (8015 g) and chloroethylacetate (10200 g) was added through the addition funnel over a 1 hour period at 0° C. to 5° C.

4. The reaction mixture was stirred for 30 minutes at 0 to 5° C.

5. The reaction mixture was allowed to warm to room temperature.

6. The reaction mixture was stirred for 6 to 18 hours at RT.
7. The reaction was monitored by GC.
8. The reaction mixture was cooled to 5-10° C. once the reaction was complete by GC analysis.
9. Water (51 L) was added over a minimum of 30 minutes at below 10° C.
10. The reaction mixture was stirred for 30 minutes at 5-10° C.
11. The reaction mixture was neutralized with conc. HCl (approximately 8 L) at below 10° C. until reaching pH 1-2.
12. The reaction mixture was warmed to room temperature (15° C. to 25° C.) and stirred for 30 minutes at RT.
13. The layers were separated and the top organic layer containing the product was collected. The lower aqueous layer was extracted with MTBE (51 L).
14. The two organic layers were combined and the lower aqueous layer was discarded.
15. The combined organic layer was washed with brine solution (51 L).
16. The MTBE was removed under vacuum with a jacket temp of 20-25° C. to minimum stir volume.
17. The vacuum was discontinued and ethanol (51 L) was added to the reaction mixture. The remaining MTBE was distilled under atmospheric pressure until the internal temperature of the reaction mixture reached 70-78° C.
18. This reaction mixture in ethanol was used for the next step with out further purification to give compound 5 as a pale yellow to brownish liquid (12530 g, assuming 100% yield).

Example 4

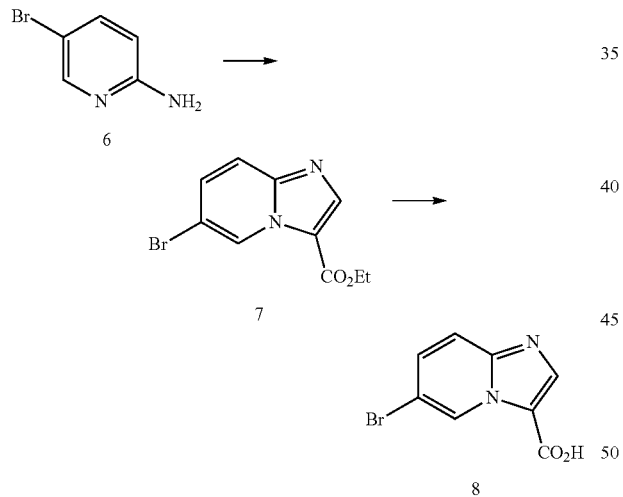

Preparation of compound 8:
1. An ethanol solution of compound 5 (12400 g in 51 L of ethanol) was added to an appropriately sized stainless steel reactor at room temperature under nitrogen atmosphere.
2. Compound 6 (9500 g) was added as a solid in one portion at room temperature.
3. The reaction mixture was heated to reflux (~78° C.) and stirred for 1-2 days.
4. The reaction was monitored by HPLC.
5. Upon completion, the reaction mixture was allowed to cool to room temperature.
6. NaOH solution (9884 g solid pellets dissolved in 38 L of water) was added as a stream over a 30 min period at an internal temperature below 35° C.
7. The reaction mixture was heated to reflux (~78° C.) for 3 to 4 hours.
8. The reaction was monitored by HPLC.
9. Upon completion, the reaction mixture was cooled to an appropriate temperature to start solvent removal.
10. All ethanol (approximately 5 volumes of ethanol) was removed under vacuum at 40 to 45° C.
11. The reaction mixture was cooled to room temperature.
12. Water (57 L; 6 vol) was added at room temperature.
13. The aqueous solution was washed with ethyl acetate (2×38 L) to remove all organic impurities.
14. The lower aqueous layer was cooled to 0-5° C. and acidified with conc. HCl (~15 L) until reaching pH 1-2.
15. The reaction mixture was stirred for 1 to 2 hours at 0 to 5° C.
16. The mixture was filtered and the cake was washed with water (2×38 L) and acetone (2×19 L) followed by drying for 1-2 hours.
17. The solid collected was transferred back into an appropriately sized reactor.
18. Heptane (95 L; 10 vol) was added to the reactor; the suspension was stirred for 4 to 5 hours at room temperature.
19. The solid was collected by filtration and washed with heptane (2×19 L).
20. The solid (15 kg) was suspended in methanol (75 L; 5 vol) at room temperature for 2 hours.
21. The suspension was filtered and the solid collected was washed with methanol (2×5 L).
22. The solid was dried under vacuum at 50° C. to constant weight to give compound 8 as an off-white to white solid (10169 g, 83.3% yield; HPLC purity 99.2%; $^1$HNMR (DMSO-d6, 300 MHz) δ 9.4 (s, 1H), 8.3 (s, 1H), 7.85-7.67 (m, 2H)).

Example 5

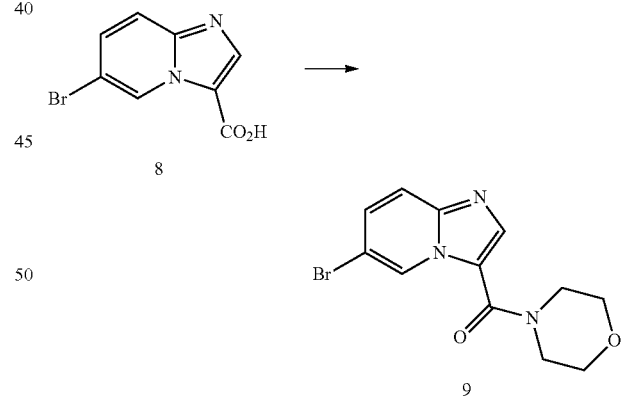

Synthesis of compound 9:
1. An appropriately sized round bottom flask (5 L) was equipped with a mechanical stirrer, thermocouple, addition funnel, nitrogen inlet and a cooling bath.
2. The flask was charged with dioxane (2.73 L) and compound 8 (273 g) at room temperature under a nitrogen atmosphere.
3. The resulting slurry was stirred for 15 minutes at room temperature.
4. DMF (8.3 g) was added at room temperature.
5. The reaction mixture was cooled to 0° C. to 5° C.

6. Thionyl Chloride (269 g) was slowly added via the addition funnel to the reaction mixture, maintaining an internal temperature between 0° C. to 5° C. The addition funnel was rinsed with a minimum amount of 1,4-Dioxane (135 mL; 0.5 vol).

7. The reaction mixture was heated to reflux (98° C. to 102° C.) and stirred for 12 to 20 hours.

8. The reaction progress was monitored by HPLC.

9. Upon completion, the reaction mixture was cooled to 0° C. to 10° C.

10. Morpholine (492 g) was added slowly via the addition funnel to the reaction mixture, maintaining an internal temperature between 0° C. to 10° C. under a nitrogen atmosphere.

11. The reaction mixture was warmed to room temperature and stirred at room temperature for 12 to 18 hours.

12. Progress of the reaction was monitored by HPLC.

13. Upon completion, the solvent was removed under vacuum at <50° C. to 3 volumes based on compound 8 to give a thick slurry.

14. The slurry was transferred into a round bottom flask and cooled to room temperature.

15. Water (5.46 L) was added at room temperature.

16. The resulting mixture was stirred for 3 hours at room temperature.

17. The solid was collected by filtration and washed with water (2×1.4 L) and heptane (2×1.4 L).

18. The solid was dried under vacuum at 50° C. to constant weight to give compound 9 as a beige solid (296 g, 84% yield; HPLC purity 99.5%; $^1$HNMR (DMSO-d6, 300 MHz) δ 9.2 (s, 1H), 7.8 (s, 1H), 7.58-7.5 (d, 1H), 7.45-7.38 (d, 1H), 3.9-3.7 (m, 8H)).

Example 6

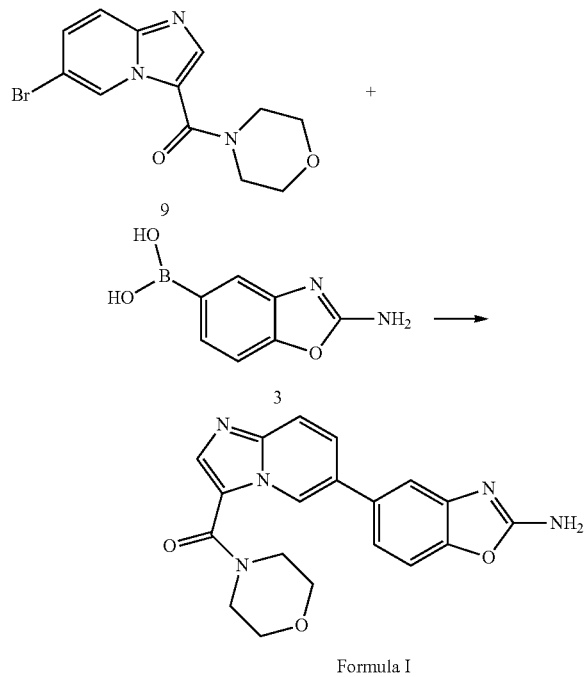

Formula I

Preparation of (6-(2-aminobenzo[d]oxazol-5-yl)imidazo[1,2-a]pyridin-3-yl)(morpholino)methanone (Formula I):

1. A 5 L three-neck round bottom flask was equipped with a mechanical stirrer, thermocouple probe, Nitrogen/vacuum inlet and reflux condenser and placed into a heating mantle.

2. 1,4-Dioxane (3.75 L) and water (1.25 L) were added at room temperature.

3. Compound 9 (250 g) and Compound 3 (210 g) were added to the flask at room temperature.

4. The reaction mixture was stirred for 10 min at room temperature.

5. Sodium carbonate (300 g) was added to the flask followed by Pd(PPh$_3$)$_4$ (47 g) under nitrogen at room temperature.

6. With stirring, the reactor was sparged with nitrogen for ~30 minutes at <20° C.

7. The reaction mixture was deoxygenated by performing 5 to 6 vacuum/nitrogen cycles.

8. The reaction mixture was heated to reflux (88° C. to 102° C.) under slight nitrogen bubbling and stirred for 5 to 8 hours.

9. The reaction was monitored by HPLC.

10. Upon completion, the reaction mixture was cooled to 75-80° C.

11. Water (3.75 L) and ethyl acetate (1.25 L) were added to the reaction mixture at 75-80° C.

12. The resulting mixture was cooled to room temperature and stirred for 2 hours at room temperature.

13. The mixture was filtered and the solid collected was washed with water (2×1.25 L), methanol (1.25 L) and ethyl acetate (2×1.25 L).

14. The solid was suspended in ethyl acetate (1.5 L) at room temperature for 1 hour.

15. The suspension was filtered and the solid collected was washed with ethyl acetate (250 mL).

16. This process was repeated two more times.

17. The solid obtained was dried under vacuum to give a crude product (250 g, 85% yield; HPLC purity 98.1%; Pd level 1831 ppm).

Further purification of the crude product:

18. The crude product (250 g) was suspended in methanol (2.5 L) and HCl (158 mL) at room temperature.

19. The mixture was heated to 40 to 45° C. to give a slightly cloudy solution.

20. Charcoal (250 g) was added to the reaction mixture at 40 to 45° C.

21. The resulting mixture was stirred for 30 minutes at 40 to 45° C.

22. The hot solution was filtered through a poly pad with 2 inch celite bed and the cake was washed with methanol (3×500 mL).

23. The solution was recharged to the flask (Pd level: 330 ppm).

24. The solution was heated to 40 to 45° C.

25. Charcoal (50 g) and silica thiol (50 g) were added at 40 to 45° C.

26. The mixture was stirred for 30 minutes at 40 to 45° C.

27. The hot solution was filtered through a poly pad and the cake was washed with methanol (250 mL)

28. This process was repeated one more time.

29. The methanol was removed under vacuum at 30-35° C. to ~2.5 L.

30. The solution was cooled to 10 to 15° C.

31. Concentrated aqueous ammonia solution (200 mL) was added until reaching pH 8-9.

32. The reaction mixture was cooled to 0 to 5° C. and stirred for 1 to 2 hours at 0 to 5° C.

33. The mixture was filtered and the cake was washed with water (2×500 mL) and methanol (2×500 mL).

34. The solid collected was transferred back into a round bottom flask and suspended in ethyl acetate (2.5 L) at room temperature for 2 to 3 hours.

35. The solid was collected by filtration and washed with ethyl acetate (750 mL).

36. The solid was dried under vacuum at ~50° C. to constant weight to give the compound of Formula I as an off-white solid (180 g, 61% yield; HPLC purity 98.5%; $^1$HNMR (DMSO-d6, 300 MHz) δ 9.1 (s, 1H), 8.1 (s, 1H), 7.8-7.65 (2H), 7.60-7.40 (m, 4H), 7.3-7.2 (1H), 3.8-3.6 (m, 8H); Pd level 1 ppm).

Example 7

Instrument and Methodology Details

GVS

Sorption isotherms were obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen, with a total flow rate of 200 mL.min−1 The relative humidity was measured by a calibrated Rotronic probe (dynamic range of 1.0-100% RH), located near the sample. The weight change (mass relaxation) of the sample as a function of % RH was constantly monitored by the microbalance (accuracy±0.005 mg).

Approximately 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.0.0.7.

FIG. 14 shows a GVS isotherm plot of scaled-up HCl Pattern 2.

XRPD

X-Ray Powder Diffraction patterns were collected either on a Bruker AXS C2 GADDS diffractometer or a Bruker AXS D8 diffractometer. On a Bruker AXS C2 GADDS diffractometer, the following parameters were used: Cu Kα radiation (40 kV, 40 mA), automated XYZ stage, laser video microscope for auto-sample positioning and a HiStar 2-dimensional area detector. X-ray optics consisted of a single Gobel multilayer mirror coupled with a pinhole collimator of 0.3 mm. A weekly performance check was carried out using a certified standard NIST 1976 Corundum (flat plate).

The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. In a typical experiment, the sample is exposed to the X-ray beam for 120 seconds. The software used for data collection was GADDS for WNT 4.1.16 and the data were analyzed and presented using Diffrac PlusEVA v11.0.0.2 or v13.0.0.2.

Ambient Conditions

Samples run under ambient conditions were prepared as flat plate specimens using powder as received without grinding. Approximately 1-2 mg of the sample was lightly pressed on a glass slide to obtain a flat surface.

Non-Ambient Conditions

Samples run under non-ambient conditions were mounted on a silicon wafer with heat-conducting compound. The sample was then heated to the appropriate temperature at 10.C.min$^{-1}$ and subsequently held isothermally for 1 minute before data collection was initiated.

On a Bruker D8 diffractometer, the following parameters were used: Cu Kα radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analyzed and presented using Diffrac Plus EVA v11.0.0.2 or v13.0.0.2.

Samples were run under ambient conditions as flat plate specimens using powder as received. The sample was gently packed into a cavity cut into polished, zero-background (510) silicon wafer. The sample was rotated in its own plane during analysis. The details of the data collection are:

Angular range: 2 to 42° 2θ

Step size: 0.05° 2θ

Collection time: 0.5 s/step

XRPD Patterns for HCl Pattern 1, HCl Pattern 2, HBr Pattern 1, HBr Pattern 2, HBr Pattern 3 are shown in FIGS. 1, 2, 7, 10, and 13, respectively.

Nuclear Magnetic Resonance ($^1$H-NMR)

Figure 3:
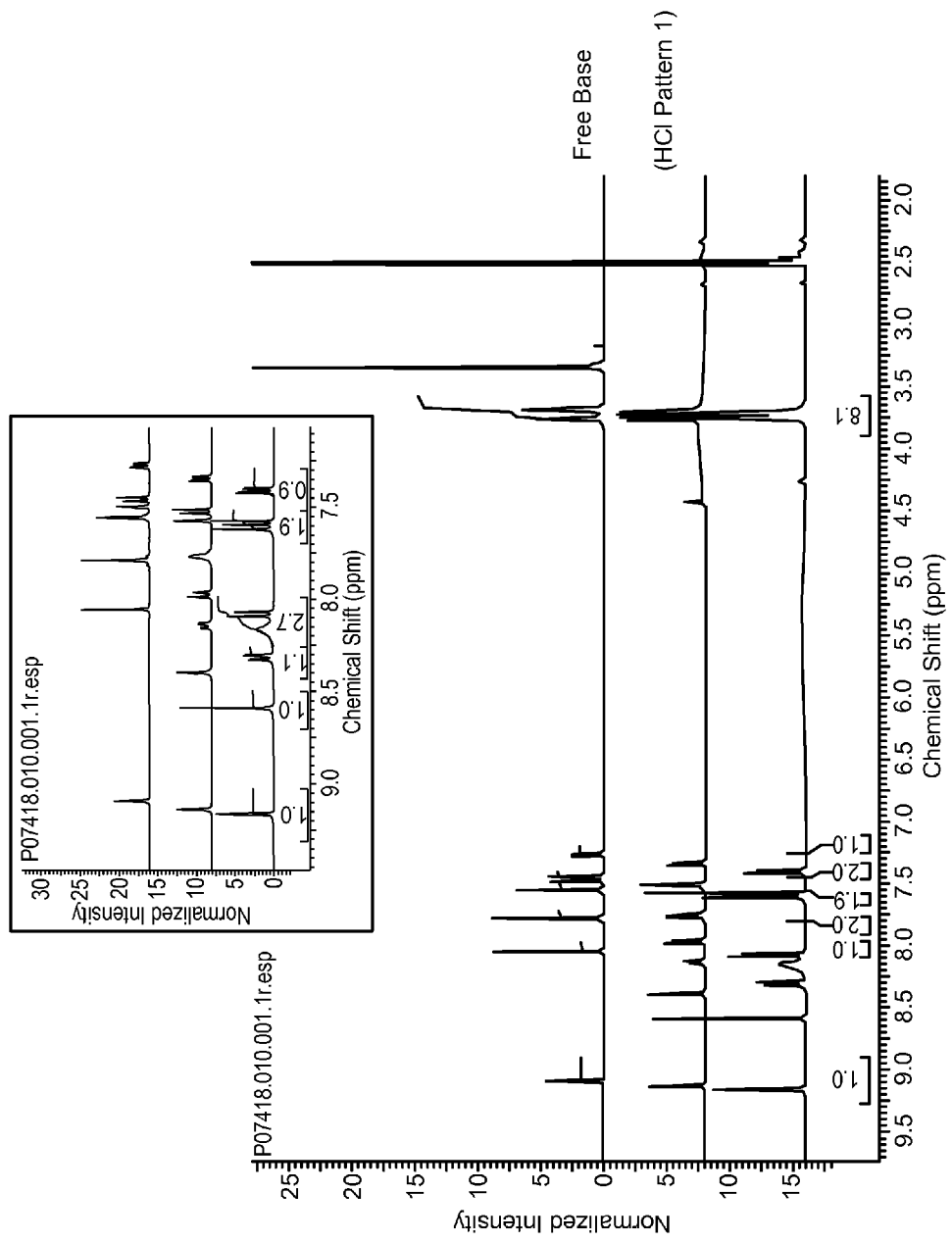
FIG. 3 shows $^1$H NMRs of HCl Pattern 1 and HCl Pattern 2.
Figure 8:
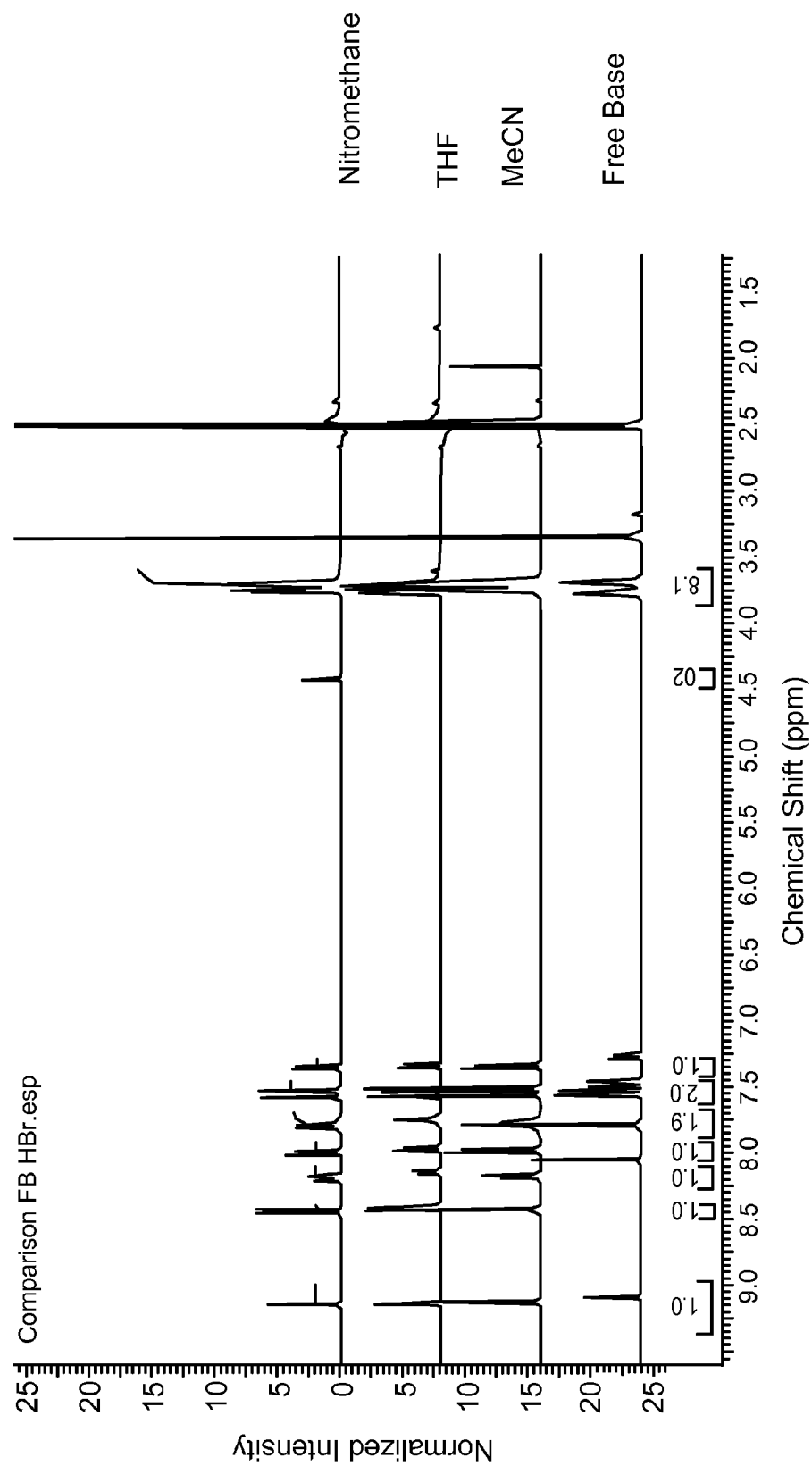
FIG. 8 shows a $^1$H NMR of HBr Pattern 1.
Figure 11:
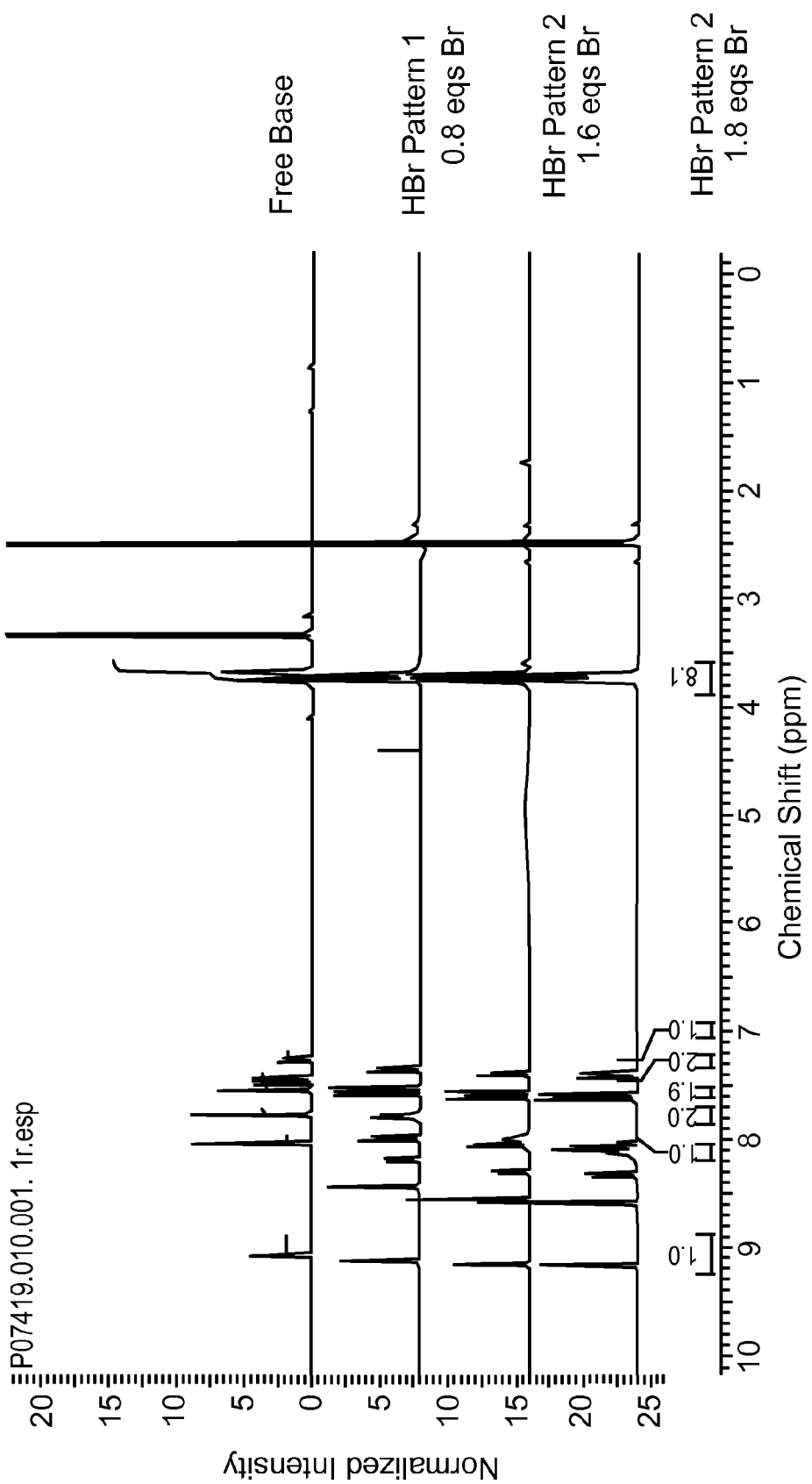
FIG. 11 shows $^1$H NMRs of HBr Pattern 2.

NMR spectra were collected on a Bruker 400 MHz instrument equipped with an auto-sampler, and controlled by a DRX400 console. Automated experiments were acquired using ICON-NMR v4.0.4 running with Topspin v1.3 using the standard Bruker loaded experiments. For non-routine spectroscopy, data were acquired through the use of Topspin alone. $^1$H-NMR spectra for HCl Pattern 1 and HCl Pattern 2 are shown in FIG. 3. $^1$H-NMR spectra for HBr Pattern 1 and HBr Pattern 2 are shown in FIGS. 8 and 11, respectively.

Differential Scanning Calorimetry (DSC)

DSC data were collected on a TA Instruments Q2000 equipped with a 50 position auto-sampler. The calibration for thermal capacity was carried out using sapphire and the calibration for energy and temperature was carried out using certified indium.

Typically 0.5-3 mg of each sample, in a pin-holed aluminum pan, was heated at 10° C.·min$^{-1}$ from 25° C. to 300° C. A purge of dry nitrogen at 50 mL·min$^{-1}$ was maintained over the sample.

The instrument control software was Advantage for Q Series v2.8.0.392 and Thermal Advantage v4.8.3 and the data were analyzed using Universal Analysis v4.4A.

Figure 9:
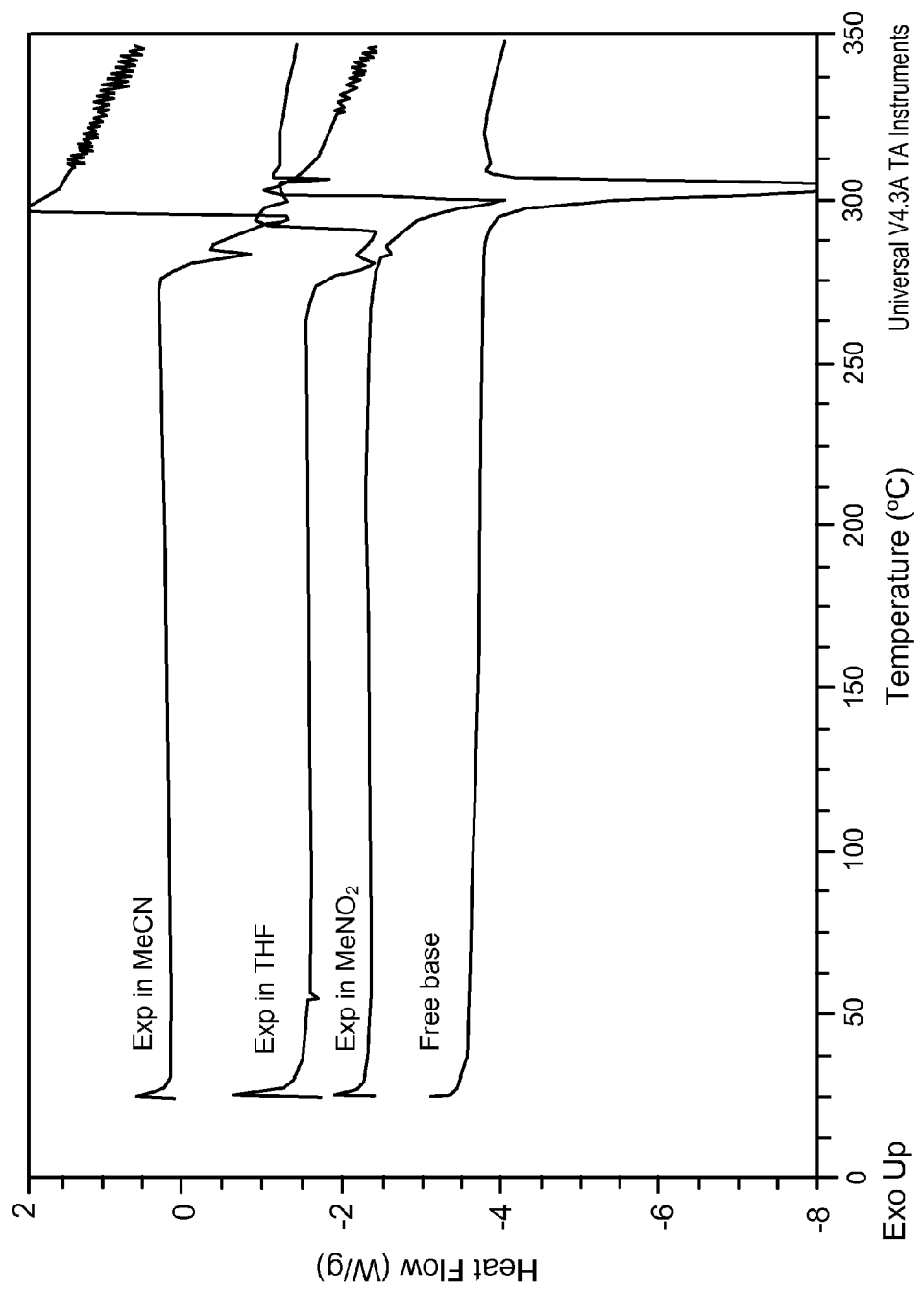
FIG. 9 shows DSC traces of HBr Pattern 1.
Figure 10:
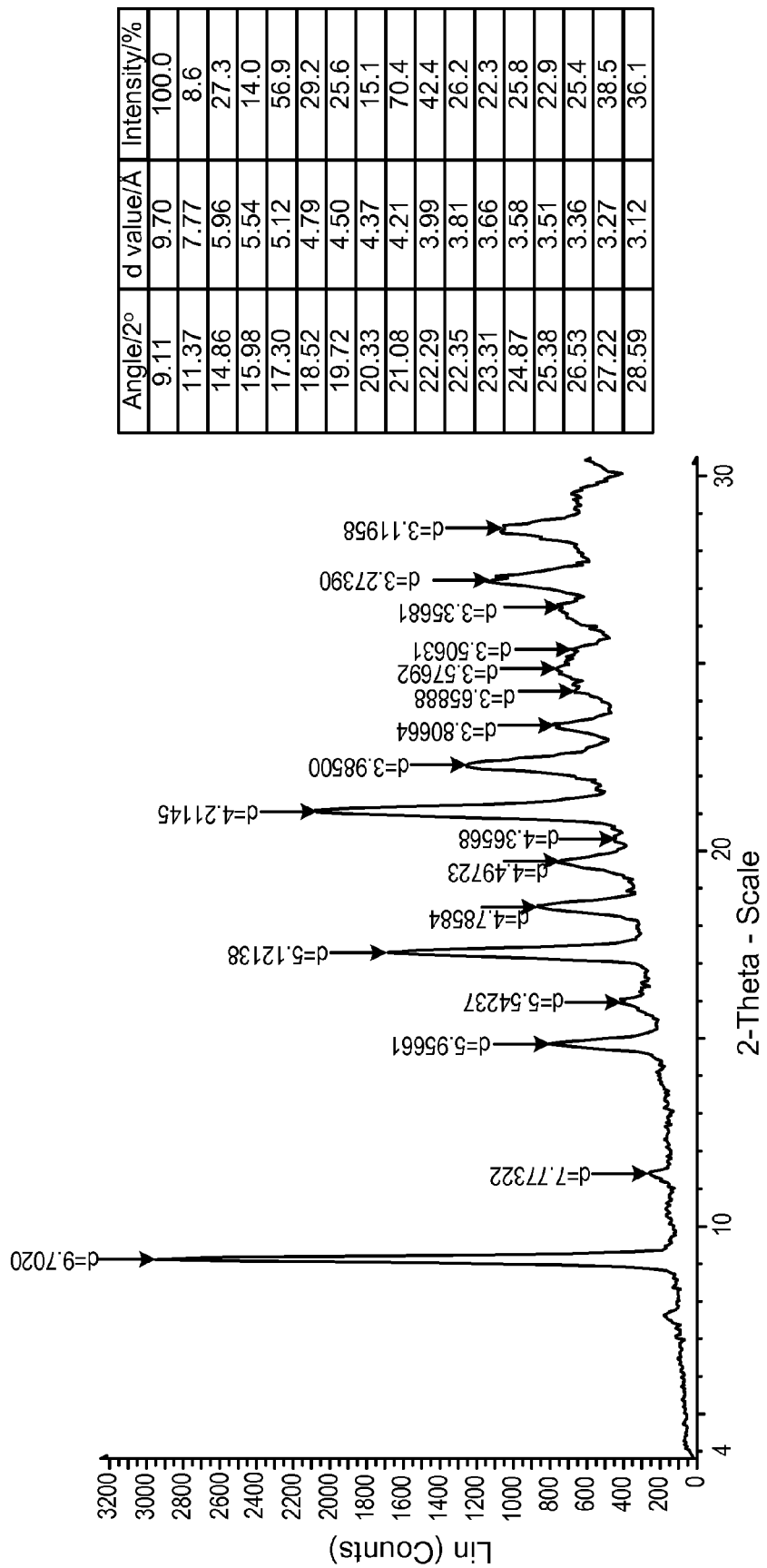
FIG. 10 shows XRPD patterns of HBr Pattern 2.

DSC traces for HCl Pattern 2 and HBr Pattern 1 are shown in FIGS. 5 and 9, respectively.

Thermo-Gravimetric Analysis (TGA)

TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminum DSC pan and heated at 10° C.·min$^{-1}$ from ambient temperature to 350° C. A nitrogen purge at 60 mL·min$^{-1}$ was maintained over the sample.

The instrument control software was Advantage for Q Series v2.8.0.392 and Thermal Advantage v4.8.3 and the data were analyzed using Universal Analysis v4.4A.

FIG. 4 shows a TGA trace for HCl Pattern 2.

Ion Chromatography (IC)

Data were collected on a Metrohm 861 Advanced Compact IC using IC Net software v2.3. Accurately weighed samples were prepared as stock solutions in an appropriate dissolving solution and diluted appropriately prior to testing. Quantification was achieved by comparison with standard solutions of known concentration of the ion being analyzed.

TABLE 1

IC Method Parameters for Anion Chromatography

| Type of method | Anton exchange |
| --- | --- |
| Column | Metrosep A Supp 5-250 (4.0 × 250 mm) |
| Column Temperature (° C.) | Ambient |
| Injection (μL) | 20 |
| Detection | Conductivity detector |
| Flow Rate (mL/min) | 0.7 |
| Eluent | 3.2 mM sodium carbonate, 1.0 mM sodium hydrogen carbonate in 5% aqueous acetone. |

Example 8

Salt Selection

Preparation of the hydrochloride salt was performed in the 20 solvents used for the solubility screen in order to select the optimal solvents for the salt screen. Formula I free base (ca. 10 mg) was suspended in the selected solvents (50 volumes; 500 μL) with stirring at 40° C. HCl (1.1 equivalents; 29 μL of 1M solution in THF) was added, and the temperature was maintained for 30 minutes. The vials were subjected to heating/cooling cycles between room temperature and 50° C., four hours at each condition. After 1 day, an aliquot of each experiment was taken, isolated by vacuum filtration, dried by suction and analyzed by XRPD. The experiments were left cycling for further three days. An aliquot of each experiment was taken, isolated by vacuum filtration, dried by suction and analyzed by XRPD. Results are summarized in Table 2.

TABLE 2

Results of HCl salt screen from 20 different solvents

| Entry | Solvent | Appearance on addition of acid | XRPD post 1 day maturation | XRPD post 4 days maturation | Other analysis |
| --- | --- | --- | --- | --- | --- |
| -01 | Methanol | Suspension | New peaks + free base (loss of crystallinity) | Loss of crystallinity | Shifts suggest salt by $^1$H-NMR |
| -02 | Ethanol | Suspension | New peaks + free base (loss of crystallinity) | Amorphous | n/a |
| -03 | IPA | Suspension | New peaks + free base (loss of crystallinity) | Amorphous | n/a |
| -04 | Acetonitrile | Suspension | New peaks + free base | HCl Pattern 1 | Shifts suggest salt by $^1$H-NMR |
| -05 | Acetone | Suspension | New peaks + free base | Free base | n/a |
| -06 | MEK | Suspension | New peaks + free base | HCl Pattern 1 | Shifts suggest salt by $^1$H-NMR |
| -07 | MIBK | Suspension | New peaks + free base | New peaks + free base | n/a |
| -08 | EtOAc | Suspension | New peaks + free base (loss of crystallinity) | New peaks + free base | n/a |
| -09 | IPAc | Suspension | New peaks + free base (loss of crystallinity) | New peaks + free base | n/a |
| -10 | DIPE | Suspension | New peaks + free base | New peaks + free base | n/a |
| -11 | TBME | Suspension | New peaks + free base | New peaks + free base | n/a |
| -12 | THF | Suspension | New peaks + free base (loss of crystallinity) | HCl Pattern 1 | Shifts suggest salt by $^1$H-NMR |
| -13 | 1-4-Dioxane | Suspension | New peaks + free base (loss of crystallinity) | Amorphous | n/a |
| -14 | MeNO$_2$ | Suspension | HCl Pattern I | n/a | Shifts suggest salt by $^1$H-NMR (0.1 eqs residual solvent) |
| -15 | Toluene | Suspension | New peaks + free base | New peaks + free base | Shifts suggest salt by $^1$H-NMR |
| -16 | BuOAc | Suspension | New peaks + free base (loss of crystallinity) | New peaks + free base (loss of crystallinity) | n/a |
| -17 | DCM | Suspension | New peaks + free base (loss of crystallinity) | New peaks + free base (loss of crystallinity) | n/a |
| -18 | tBuOH | Suspension | New peaks + free base | Free base | |

TABLE 2-continued

Results of HCl salt screen from 20 different solvents

| Entry | Solvent | Appearance on addition of acid | XRPD post 1 day maturation | XRPD post 4 days maturation | Other analysis |
|---|---|---|---|---|---|
| -19 | NMP | Solution | n/a (evaporation yielded oil) | n/a | n/a |
| -20 | DMSO | Solution | n/a (evaporation yielded oil) | n/a | n/a |

Formula I free base (ca. 30 mg) was suspended in selected solvents (THF, nitromethane, acetonitrile and MEK; 50 volumes, 1.5 mL) at 50° C. with stirring. The corresponding acid (1 equivalent) was added and the samples were stirred for 30 minutes, prior to ramping at 1° C.·min$^{-1}$ to 25° C. The samples were placed in a shaker and subjected to heating/cooling cycles, between room temperature and 50° C., with four hours at each condition. Details about the acids used for these experiments, including input materials and amounts, are summarized in Table 3 below.

TABLE 3

Input materials used for the salt screen

| Entry | Acid | Stock solution | Amount |
|---|---|---|---|
| -01 | Hydrochloric acid | 1M in THF | 83 μl |
| -02 | Sulfuric acid | 1M in THF | 83 μl |
| -03 | 1-2-Ethane disulfonic acid | 1M in THF | 83 μl |
| -04 | p-Toluene sulfonic acid | 1M in EtOH | 83 μl |
| -05 | Methane sulfonic add | 1M in THF | 83 μl |
| -06 | Benzene sulfonic acid | 1M in THF | 83 μl |
| -07 | Oxalic acid | 1M in THF | 83 μl |
| -08 | 2-Hydroxy ethanesulfonic acid | Added as Na salt with 1 equivalent of HCl (1M solution in THF) | 12.2 mg in 83 μl solution in THF |
| -09 | L-Aspartic acid | Added as solid | 10.99 ing |
| -10 | Maleic acid | 1M in THF | 83 μl |
| -11 | Phosphoric acid | 1M in THF | 83 μl |
| -12 | Ethane sulfonic acid | 1M in THF | 83 μl |
| -13 | Hydrobromic acid | 1M in THF | 83 μl |
| -14 | Naphthalene sulfonic acid | Added as Na salt with 1 equivalent of HCl (1M solution in THF) | 20.9 mg in 83 μl solution in THF |
| -15 | Naphthalene di-sulfonic acid | Added as Na salt with 2 equivalents of HCl (1M solution in THF) | 28.9 mg in 166 μl solution in THF |

After 16 hours, an aliquot was taken, isolated by vacuum filtration, dried by suction and analyzed by XRPD. Further solvent (25 volumes) was added, and the suspensions were allowed to cycle for four more days. An aliquot was taken, isolated by vacuum filtration, dried by suction and analyzed by XRPD. Further acid (0.2 equivalents, 17 μL) and solvent (25 volumes) were added to those samples showing the presence of free base in the XRPD pattern, suggesting incomplete salt formation. The samples were stored in a shaker and subjected to heating/cooling cycles, between room temperature and 50° C., with four hours at each condition for one week. An aliquot was taken, isolated by vacuum filtration, dried by suction and analyzed by XRPD. Water (10% for MeCN, and 5% for THF, MEK and nitromethane, based on ca. 1.5 mL solvent) was added and the samples were cycled for a further 5 days. An aliquot was taken, isolated by vacuum filtration, dried by suction and analyzed by XRPD.

For samples exhibiting new XRPD patterns, the remaining solid was isolated by vacuum filtration, dried by suction and further characterization was undertaken as follows.

TABLE 4

XRPD results from the salt screen in acetonitrile.

| Entry | On acid addition | Post 3 days maturation | Post addition of +25 vols solvent | +0.2 eqs acid + 25 vols solvent | +10% water |
|---|---|---|---|---|---|
| -01 | Suspension | HCl1 + FB | HCl1 + FB | HCl 1 + FB | Partially crystalline HCl 1 |

TABLE 4-continued

XRPD results from the salt screen in acetonitrile.

| Entry | On acid addition | Post 3 days maturation | Post addition of +25 vols solvent | +0.2 eqs acid + 25 vols solvent | +10% water |
|---|---|---|---|---|---|
| -02 | Suspension | Partially crystalline FB | Partially crystalline FB | Amorphous | Amorphous |
| -03 | Suspension | FB | Partially crystalline FB | Partially crystalline FB | Amorphous |
| -04 | Suspension | New peaks + FB | New peaks, ISOLATED | n/a | n/a |
| -05 | Suspension | New peaks + FB | New peaks + FB | New peaks + FB | Insufficient solid |
| -06 | Suspension | FB | FB | FB | FB |
| -07 | Suspension | New peaks + FB | New peaks + FB | New peaks + FB | FB |
| -08 | Suspension | New peaks + HCl1 + FB | New peaks + HCl1 + FB | New peaks + HCl1 + FB | n/a |
| -09 | Suspension | FB + acid | FB + acid | FB + acid | FB + acid |
| -10 | Suspension | FB | FB | FB | FB |
| -11 | Suspension | New peaks + FB | n/a | New peaks + FB | New peaks + FB |
| -12 | Suspension | FB | n/a | New peaks + FB | New peak + FB |
| -13 | Suspension | Partially crystalline - new peaks ISOLATED | n/a | n/a | n/a |
| -14 | Suspension | New peaks + HCl1 + FB | n/a | New peaks + HCl1 + FB | n/a |
| -15 | Suspension | HCl1 + FB | n/a | HCl1 + FB | n/a |

TABLE 5

XRPD results from the salt screen in MEK

| Entry | On acid addition | Post 3 days maturation | Post addition of +25 vols solvent | +0.2 eqs acid + 25 vols solvent | +5% water |
|---|---|---|---|---|---|
| -01 | Suspension | HCl 1 + FB | n/a | HCl 1 | Oil |
| -02 | Suspension | Partially crystalline FB | n/a | Amorphous | Oil |
| -03 | Suspension | FB | n/a | Partially crystalline FB + new peaks | Oil |
| -04 | Suspension | New peaks + FB | n/a | New peaks + FB | Oil |
| -05 | Suspension | New peaks + FB | n/a | FB | Sticky solid |
| -06 | Suspension | FB | n/a | Amorphous | Gum |
| -07 | Suspension | New peaks ISOLATED | n/a | n/a | n/a |
| -08 | Suspension | New peaks + HCl1 + FB | n/a | Partially crystalline - new peaks + FB | Gum |
| -09 | Suspension | FB + acid | n/a | FB + acid | Sticky solid |
| -10 | Suspension | FB | n/a | FB | Sticky solid |
| -11 | Suspension | New peaks + FB | n/a | Partially crystalline - new peaks + FB | Oil |
| -12 | Suspension | New peaks + FB | n/a | New peaks + FB | Oil |
| -13 | Suspension | New peaks + FB | n/a | n/a | n/a |
| -14 | Suspension | New peaks + HCl1 + FB | n/a | Amorphous | Oil |
| -15 | Suspension | New peaks + HCl1 + FB | n/a | HCl 1 + FB | Sticky solid |

TABLE 6

XRPD results from the salt screen in THF

| Entry | On acid addition | Post 3 days maturation | Post addition of +25 vols solvent | +0.2 eqs acid + 25 vols solvent | +5% water |
|---|---|---|---|---|---|
| -01 | Suspension | HCl 1 ISOLATED | n/a | n/a | n/a |

TABLE 6-continued

XRPD results from the salt screen in THF

| Entry | On acid addition | Post 3 days maturation | Post addition of +25 vols solvent | +0.2 eqs acid + 25 vols solvent | +5% water |
|---|---|---|---|---|---|
| -02 | Suspension | New peaks + FB | n/a | Partially crystalline - new peaks + FB | Oil |
| -03 | Suspension | FB | n/a | Amorphous | Oil |
| -04 | Suspension | Amorphous | n/a | New peaks + FB | Oil |
| -05 | Suspension | New peaks + FB | n/a | Amorphous | Gum |
| -06 | Suspension | FB | n/a | FB | Gum |
| -07 | Suspension | FB | n/a | FB | Sticky solid |
| -08 | Suspension | New peaks + FB | n/a | New peaks + FB | Gum |
| -09 | Suspension | FB + acid | n/a | FB + acid | Sticky solid |
| -10 | Suspension | FB | n/a | FB | Sticky solid |
| -11 | Suspension | New peaks + FB | n/a | Partially crystalline - new peaks + FB | Gum |
| -12 | Suspension | New peaks + FB | n/a | New peaks + FB | Oil |
| -13 | Suspension | New pattern ISOLATED | n/a | n/a | n/a |
| -14 | Suspension | New peaks + HCl 1 + FB | n/a | New peaks + FB | Oil |
| -15 | Suspension | New peaks + HCl 1 + FB | n/a | HCl 1 + FB | Sticky solid |

TABLE 7

XRPD results from the salt screen in nitromethane

| Entry | On acid addition | Post 3 days maturation | Post addition of +25 vols solvent | +0.2 eqs acid + 25 vols solvent | +5% water SDR-714-24D |
|---|---|---|---|---|---|
| -01 | Suspension | HCl 1 | HCl 1 ISOLATED | n/a | n/a |
| -02 | Suspension | Amorphous | Amorphous | Gum | Oil |
| -03 | Suspension | Partially crystalline FB | FB | New peaks + FB | Oil |
| -04 | Suspension | FB | New peaks + FB | Amorphous | Oil |
| -05 | Suspension | New peaks + FB | Amorphous | Partially crystalline FB | Gum |
| -06 | Suspension | FB | FB | FB | Amorphous |
| -07 | Suspension | New peaks + FB | New peaks + FB | New peaks + FB | New peaks + FB |
| -08 | Suspension | New peaks + FB | New peaks + HCl 1 + FB | Gum | n/a |
| -09 | Suspension | FB + acid | FB + acid | FB + acid | FB + acid |
| -10 | Suspension | New peaks + FB | FB | Partially crystalline FB | n/a |
| -11 | Suspension | New peaks + FB | New peaks + FB | Gum | Oil |
| -12 | Suspension | FB | FB | Oil | Oil |
| -13 | Suspension | New pattern | New pattern ISOLATED | n/a | n/a |
| -14 | Suspension | New peaks + FB | New peaks + FB | Gum | Insufficient solid |
| -15 | Suspension | Amorphous | Amorphous | Gum | Sticky solid |

The highlighted samples were filtered under suction and dried under vacuum at room temperature for ca. 68 hours. The solids obtained from HCl and HBr were characterized by XRPD, $^1$H-NMR, DSC and Ion Chromatography and the results from these are discussed as follows.

Formula I HCl salt was obtained by maturation with additional solvent in nitromethane.

TABLE 8

Analysis of HCl salt from nitromethane

| Analysis | Details |
|---|---|
| XRPD (vacuum dried) | HCl Pattern 1 |
| $^1$H-NMR | Consistent with salt formation, no residual solvent |
| DSC | Several endothermic events, consistant with results from solvent screen |
| Ion Chromatography | 0.8 eqs Cl |

Formula I HBr salts were obtained by maturation for 3 days in acetonitrile and THF, and by maturation with additional solvent in nitromethane.

TABLE 9

HBr salts obtained in the salt screen

| Analysis | Acetonitrile: | THF: | Nitromethane: |
|---|---|---|---|
| XRPD (vacuum dried) | HBr Pattern 1, slight evidence of FB | HBr Pattern 1 | HBr Pattern 1, slight evidence of FB |
| $^1$H-NMR | Consistent with salt 0.1 eqs residual MeCN | Consistent with salt No residual solvent | Consistent with salt 0.1 eqs MeNO$_2$ |
| DSC | Double overlapping endotherm, onset at ca. 278° C. | Double overlapping endotherm, onset at ca. 273° C. | Endotherm, onset at ca. 289° C. followed by decomposition |
| Ion Chromatography | 1.1 eqs Cl | 0.8 eqs Cl | not determined |

A summary of the XRPD data of all solids obtained in the organic solvent screen are shown in Table 10.

TABLE 10

XRPD of all solids obtained from the main salt screen

| Entry | Acid | MeCN | MEK | THF | MeNO2 |
|---|---|---|---|---|---|
| -01 | Hydrochloric acid | New pattern + free base # | New pattern + free base # | New pattern * | New pattern * |
| -02 | Sulfuric acid | Free base | Free base | New pattern + free base # | Free base |
| -03 | 1-2-Ethanedisulfonic acid | Free base | Free base | Free base | Free base |
| -04 | p-Toluene sulfonic acid | New pattern * | New pattern + free base # | Amorphous | Free base |
| -05 | Methane sulfonic acid | New pattern + free base # | New patient + free base # | New pattern + free base # | New pattern + free base # |
| -06 | Benzene sulfonic acid | Free base | Free base | Free base | Free base |
| -07 | Oxalic acid | New pattern + free base # | New pattern * | Free base | New pattern + free base # |
| -08 | 2-Hydroxy ethanesulfonic acid | New pattern + free base + HCl salt # | New pattern + free base + HCl salt # | New pattern + free base # | New pattern + free base # |
| -09 | L-Aspartic acid | New pattern + free base + acid # | Free base + acid | Free base + acid | Free base + acid |
| -10 | Maleic acid | Free base | Free base | Free base | New pattern + free base # |
| -11 | Phosphoric acid | New pattern + free base # | New pattern + free base # | New pattern + free base # | New pattern + free base # |
| -12 | Ethane sulfonic acid | Free base | New pattern + free base # | New pattern + free base # | Free base |
| -13 | Hydrobromic acid | New pattern* | New pattern + free base # | New pattern * | New pattern * |
| -14 | Naphthalene sulfonic acid | New pattern + free base + HCl salt # | New pattern + free base # | New pattern + free base # | New pattern + free base + HCl salt # |
| -15 | Naphthalene di-sulfonic acid | Free base + HCl salt | New pattern + free base + HCl salt # | New pattern + free base + HCl salt # | Amorphous |

Key:
* Significantly Different XRPD pattern
Mixture new pattern + free base/acid
No new peaks - either free base or mixtures free base/acid An aqueous screen was performed. Formula I free base (ca. 30 mg) was slowly added into acidic solutions containing the corresponding acid (1.2 equivalents) in water (50 volumes), at 50° C., yielding white suspensions, which were subjected to heating/cooling cycles between room temperature and 50° C., four hours under each condition for 24 hours. An aliquot was taken, isolated by vacuum filtration and dried by suction and analyzed by XRPD.

TABLE 11

Aqueous salt screen

| Entry | Acid | Appearance | XRPD |
|---|---|---|---|
| 01 | Hydrochloric acid | White suspension | Free base |
| 02 | Sulfuric acid | White suspension | Free base |

TABLE 11-continued

Aqueous salt screen

| Entry | Acid | Appearance | XRPD |
|---|---|---|---|
| 03 | 1-2-Ethane disulfonic acid | White suspension | Free base |
| 04 | p-Toluene sulfonic acid | White suspension | Free base |
| 05 | Methane sulfonic acid | White suspension | Free base |
| 06 | Benzene sulfonic acid | White suspension | Free base |
| 07 | Oxalic acid | White suspension | Free base |
| 08 | 2-Hydroxy ethanesulfonic acid | White suspension | Free base |
| 09 | L-Aspartic acid | White suspension + large crystals | Free base + acid |
| 10 | Maleic acid | White suspension | Free base |
| 11 | Phosphoric acid | White suspension | Free base |
| 12 | Ethane sulfonic acid | White suspension | Free base |
| 13 | Hydrobromic acid | White suspension | HBr Pattern 3 |
| 14 | Naphthalene sulfonic acid | Yellow suspension | Free base |
| 15 | Naphthalene di-sulfonic acid | Yellow suspension | New peaks + Free base |

The HBr sample showed a new pattern denoted as HBr Pattern 3. The remaining solid was filtered by suction, dried under vacuum at room temperature for 16 hours and characterized by XRPD, $^1$H-NMR, DSC and Ion Chromatography.

TABLE 12

Characterization of HBr salt from aqueous screen

| Analysis | Details |
|---|---|
| XRPD (vacuum dried) | HBr Pattern 3 |
| $^1$H-NMR | Consistent with salt formation, no residual solvent |
| DSC | Two broad endotherms at 66° C. and 189° C. |
| Ion Chromatography | 0.8 eqs Cl |

The preparation of salts was conducted by dissolution in concentrated aqueous inorganic acids followed by precipitation with THF. Two procedures were performed, on 10 mg or 50 mg scale, investigating the effect of the order of addition of THF on the product produced.

Procedure A: Formula I free base (ca. 10 mg) was dissolved in the corresponding concentrated acid (50 μL) with stirring at room temperature and was added dropwise over THF (500 μL). Samples using HBr and HCl yielded solids and were shaken for 10 minutes and the solid was vacuum filtered, and dried under suction. $H_3PO_4$ yielded a solution that was subjected to heating/cooling cycles between room temperature and 50° C., four hours under each condition for 7 days. Procedure B: Formula I free base (ca. 50 mg) was dissolved in the corresponding concentrated acids (250 μL) with stirring at room temperature. THF (2.5 mL) was added dropwise to the solutions, and precipitation started. The samples were shaken for 30 minutes before being placed at 2-8° C. for ca. 16 hours. HBr and HCl produced solids, which were vacuum filtered, washed with THF, dried under suction and under vacuum at 40° C. for 16 hours. Results are shown in Table 13.

TABLE 13

Results from the salt screen from concentrated aqueous acids

| Acid | Procedure | Observations after addn of THF | Maturation |
|---|---|---|---|
| HBr | A | While suspension | n/a |
| HCl | A | White suspension | n/a |
| $H_3PO_4$ | A | Solution | Oil |
| HCl | B | White suspension | n/a |
| HBr | B | White suspension | n/a |
| $H_3PO_4$ | B | Oil | n/a |

The obtained solids were characterized by XRPD, DSC, $^1$H-NMR and Ion Chromatography. The results are shown in Table 14 and Table 15 below.

TABLE 14

Characterization of HCl salts from concentrated acids

| Analysis | Details | Details |
|---|---|---|
| XRPD (air dried) | HCl Pattern 2 | HCl Pattern 2 |
| XRPD (vacuum dried) | n/a | HCl Pattern 2 Slight changes, more peaks |
| $^1$H-NMR | n/a | Consistent with salt formation Slight shifts with respect to formula I free base |
| DSC | Multiple overlapping events | Multiple overlapping events |
| Ion Chromatography | 1.6 eqs Cl | 1.7 eqs Cl |

TABLE 15

Characterization of HBr salts from concentrated acids

| Analysis | Details | Details |
|---|---|---|
| XRPD (air dried) | HBr Pattern 2 | HBr Pattern 4 |
| XRPD (vacuum dried) | n/a | HBr Pattern 4 Slight changes, more peaks |
| $^1$H-NMR | Consistent with salt 0.1 eqs residual THF | Consistent with salt Slight shifts with respect to previous batch |
| DSC | Multiple overlapping events | Multiple overlapping events |
| Ion Chromatography | 1.7 eqs Br | 1.8 eqs Br |

Hydrochloride and hydrobromide salts gave crystalline salts obtained from this screen. No difference was observed between the results from the two procedures. The ion chromatography results were consistent across the two methodologies. Formation of HCl Pattern 2 was observed using this methodology. Ion chromatography evidenced >1.5 equivalents of counter ion, equating to 2 equivalents with an estimated 15% water. Formation of two new HBr patterns was also observed, denoted HBr Pattern 2 and 4, with ion chromatography suggesting possible bis-salt formation. Analogously to HCl Pattern 2, DSC analysis of HBr Patterns 2 and 4 gave multiple overlapping endotherms, which may indicate hydrate formation (as no residual solvent was noted by NMR). Correction of the ion chromatography results taking into account the possible presence of water results in the relevant equivalents of bromide being closer to 2 equivalents.

Example 9

Scale-Up of HCl Salt Forms

HCl Pattern 1: Formula I free base (ca. 500 mg) was suspended in nitromethane (50 volumes, 25 mL) with stirring. HCl (1M in THF; 1.2 equivalents; 1.65 mL) was added. The suspension was subjected to heating/cooling cycles between RT and 50° C., 4 hours at each condition for one week. An aliquot was taken and analyzed by XRPD, which indicated that crystalline free base was still present. Further HCl (0.3 equiv, 400 µL) was added, and maturation was continued for a further week, when XRPD analysis showed the desired HCl Pattern 1. The solid was isolated by vacuum filtration and dried under vacuum at RT for 16 hours. XRPD analysis indicated the material had partially reverted to the free base, although IC suggested mono-HCl salt formation.

HCl Pattern 2: Formula I free base (ca. 500 mg) was dissolved in HCl (37% aqueous solution, 2.5 mL) with stirring for 1 hour. THF (25 mL) was added dropwise over 30 minutes. Precipitation started after ca. 5 mL THF had been added. The suspension was left stirring for five days. The solid was filtered by suction and air dried, showing a new pattern (Pattern 3) by XRPD. The solid was dried under vacuum at room temperature for ca. 16 hours, whereupon XRPD analysis confirmed the formation of HCl Pattern 2. The observed change in XRPD pattern implies HCl Pattern 3 to be an unstable salt form, possibly solvated, which converts to HCl Pattern 2 upon drying. Full characterization of HCl Pattern 2 was undertaken and details can be found in Tables 16-17 below.

TABLE 16

Characterization of scale-up HCl Pattern 2

| Experiment | Details |
| --- | --- |
| XRPD (air dried) | New pattern (HCl Pattern 3) |
| XRPD (vacuum dried) | Crystalline. HCl Pattern 2<br>Slight differences compared to HCl Pattern 2, possibly due to differences in crystallinity. |
| $^1$H-NMR | The spectrum shows shifts suggesting salt formation with no residual solvent. |
| TGA | Weight loss in three steps:<br>8% by 100° C., 2.3% to 140° C. and 8.7% to 210° C., possibly due to solvent release and dissociation |
| DSC | Multiple overlapping endothermic events. |

TABLE 17

Further Characterization of scale-up HCl Pattern 2

| Experiment | Details |
| --- | --- |
| VT-XRPD Heating to 100° C., then cool | Conversion to a new pattern at 80° C. (HCl 3), which returns to less crystalline HCl 2 upon cooling. |
| VT-XRPD Heating to 140° C. | Conversion to HCl Pattern 3 at 80° C. that remains unchanged to 120° C., before losing crystallinity at higher temperature |
| TGA heat/cool experiments | Sample heated to 100° C., cooled and re-analysed by XRPD and IC: Partially crystalline HCl Pattern 2, 1.6 eqs Cl<br>Sample heated to 140° C., cooled and re-analysed by XRPD and IC: Partially crystalline HCl Pattern 2, 1.7 eqs Cl<br>Sample heated to 210° C., decomposition observed |
| Chemical purity by HPLC | Parent purity 96.8 area %<br>Sum impurities ≥0.1% = 3.25<br>Sum impurities ≤0.1% = 0.00 |
| GVS | Reversible uptake of ca. 6 wt % between 40-90% RH.<br>Reversible dehydration observed between 30-40% RH.<br>Further reversible weight loss below 30% RH may indicate lower stoichiometry hydrate.<br>The sample contained 10.6 wt % water (3.0 eqs) at the end of the experiment, with no significant changes noted by XRPD |
| VH-XRPD | The material starts to change below 25% RH, with full conversion to HCl Pattern 3 at 0.5% RH.<br>At 13% RH the material starts to revert back to HCl Pattern 2 with complete conversion by 45% RH.<br>No change was noted between 45 and 80% RH |
| Stability at 40° C./75% RH | No significant changes observed by XRPD after 3 weeks storage |
| Thermodynamic solubility | Water: 1.6 mg · mL$^{-1}$ (pH 1.6)<br>0.1N HCl: 3.5 mg · ml$^{-1}$ (pH 0.9)<br>SGF: 2.8 mg · mL$^{-1}$ (pH 1.0) |
| IC | 1.7 eqs Cl (as determined)<br>2.0 eqs Cl (corrected with 15% w/w water content) |
| KF | 15.2% water, corresponding to 4.3 eqs water, assuming 2 eqs Cl |

HCl Pattern 2 was observed after drying under vacuum over night at room temperature, showing clear differences with respect to the wet solid. Salt formation was confirmed by $^1$H-NMR, and high chemical purity was determined by HPLC. Ion chromatography analysis, with correction for the presence of ca. 15% water, suggested formation of a bis-HCl salt. VT-XRPD showed conversion to a new pattern, given the identification of HCl Pattern 3, upon heating above 80° C., which reverted to a partially crystalline HCl Pattern 2 upon cooling to room temperature in air. Similarly, another sample that was heated to 100° C. on the TGA (8 wt % loss equates to 2.3 eqs H2O), showed less crystalline HCl Pattern 2 by XRPD upon cooling, whilst IC confirmed no loss of chloride. These suggest HCl Pattern 2 to be a hydrated form that dehydrates upon heating above 50° C. and readily re-hydrates upon cooling. A heat/cool TGA experiment to 140° C. (2.3 wt % loss equates to 0.7 eqs H$_2$O) also yielded less crystalline HCl Pattern 2 material with no loss of chloride. Further heating lead to decomposition likely due to dissociation.

GVS analysis (FIGS. 6 and 14) showed formation of a hydrated species from 30 to 40% RH, with an uptake of 10.6 wt % at the end of the analysis equating to a tri-hydrate. HCl Pattern 2 appeared to be stable to 30% RH, however dehydration was observed below 30% with rehydration occurring by 40%. Further weight loss was observed to 0% RH which may be indicative of the loss of water from the unstable mono-hydrate observed in the VT-XRPD and TGA experiments giving an unstable possibly anhydrous form. These results show the existence of two hydrated forms; tri-hydrate HCl Pattern 2 and a mono-hydrate that readily rehydrates to give HCl Pattern 2. Dehydration of the unstable mono-hydrate by heating yielded a further unstable, possibly anhydrous, material that either showed dissociation of the salt upon further heating, or rehydration to tri-hydrate HCl Pattern 2 upon cooling.

Variable humidity XRPD analysis was undertaken in order to determine if two hydrated species were present. VH-XRPD showed HCl Pattern 2 to be stable to 14% RH, whereupon the material started to change to HCl Pattern 3 with complete conversion at 0.5% RH. On increasing the humidity, the material started to re-hydrate from 13% RH, and reverted completely back to HCl Pattern 2 by 45% RH. Interestingly, and unlike VT-XRPD, no loss of crystallinity was observed upon rehydration. Only one XRPD pattern was observed upon dehydration and it is not possible to conclude whether this is a totally anhydrous or partially hydrated form. Although the sample was at 0.5% RH for 6 hours the kinetics of the VH-XRPD differs significantly from those of the GVS instrument.

In a further experiment, HCl Pattern 2 was used for a polymorphism assessment. Amorphous material was generating by starting with Pattern 2 of HCl salt of Formula I (ca. 500 mg) and suspending it in 150 mL water, resulting in a cloudy solution, which was filtered by suction. The solution was freeze-dried over night, yielding a partially crystalline HCl Pattern 2 material. The least crystalline batch of HCl Pattern 2 material was used for the polymorph assessment. Freeze-dried material (ca. 8 mg) was weighed into a vial and the selected solvent (20 vols, 200 μL) was added. The suspensions were subjected to heat/cool cycles between RT and 50° C., four hours at each condition, for three days. An aliquot was taken, isolated by vacuum filtration, dried by suction and analyzed by XRPD and the results are summarized in Table 18. Samples showed the known form HCl Pattern 2, including those in alcoholic solvents which had given amorphous material during the solvent screen, with improved crystallinity in all cases compared with the starting material.

TABLE 18

Results from the polymorph assessment

| Entry | Solvent | XRPD Result |
|---|---|---|
| -01 | MeOH | HCl Pattern 2 |
| -02 | EtOH | HCl Pattern 2 |
| -03 | IPA | HCl Pattern 2 |
| -04 | THF | HCl Pattern 2 |
| -05 | MeCN | HCl Pattern 2 |
| -06 | IPA (10% water) | HCl Pattern 2 |
| -07 | THF (5% water) | HCl Pattern 2 |
| -08 | EtOAc | HCl Pattern 2 |
| -09 | MEK | HCl Pattern 2 |
| -10 | TBME | HCl Pattern 2 |
| -11 | DCM | HCl Pattern 2 |
| -12 | Nitromethane | HCl Pattern 2 |

What is claimed is:

1. A crystalline polymorph of an HCl salt of a compound of Formula I:

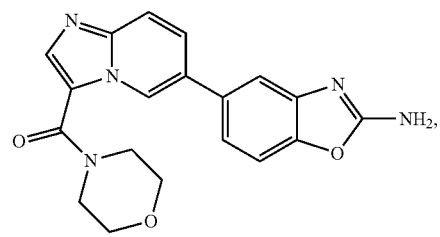

Formula I wherein said crystalline polymorph is HCl Pattern 1 characterized by X-ray powder diffraction peaks at 9.2 (±0.4) degrees, 17.5 (±0.4) degrees, 24.5 (±0.4) degrees, 27.4 (±0.4) degrees, and 28.2 (±0.4) degrees two theta.

2. The crystalline polymorph of claim 1, wherein said crystalline-polymorph is characterized by X-ray powder diffraction peaks at:

| Angle/2° |
|---|
| 9.2 |
| 14.25 |
| 14.98 |
| 16.52 |
| 17.52 |
| 19.66 |
| 19.98 |
| 21.20 |
| 21.42 |
| 22.54 |
| 23.35 |
| 23.69 |
| 24.48 |
| 26.01 |
| 27.38 |
| 28.22 |
| 29.06. |

3. A crystalline polymorph of an HCl salt of a compound of Formula I:

Formula I wherein said crystalline polymorph is HCl Pattern 2 characterized by X-ray powder diffraction peaks at 8.0 (±0.4) degrees, 16.0 (±0.4) degrees, 19.0 (±0.4) degrees, 26.5 (±0.4) degrees, and 27.7 (±0.4) degrees two theta.

4. The crystalline polymorph of claim 3, wherein said crystalline polymorph is characterized by X-ray powder diffraction peaks at:

| Angle/2° |
|---|
| 7.56 |
| 8.01 |
| 9.45 |
| 9.80 |
| 10.34 |
| 13.18 |
| 13.48 |
| 13.95 |
| 15.01 |
| 15.30 |
| 16.02 |
| 17.40 |
| 18.10 |
| 18.98 |
| 20.09 |
| 20.37 |
| 21.38 |
| 22.72 |
| 23.02 |
| 23.52 |
| 24.02 |
| 24.93 |
| 26.14 |
| 26.51 |
| 27.23 |
| 27.68 |
| 29.97 |
| 32.23. |

5. A crystalline polymorph of an HBr salt of a compound of Formula I:

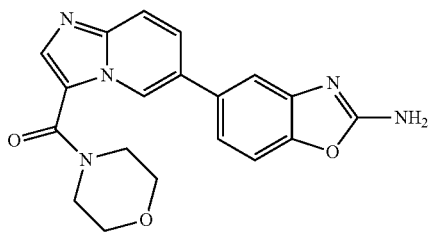

Formula I wherein said crystalline polymorph is HBr Pattern 1 characterized by X-ray powder diffraction peaks at 18.5 (±0.4) degrees, 21.6 (±0.4) degrees, 22.8 (±0.4) degrees, and 26.1 (±0.4) degrees two theta.

6. The crystalline polymorph of claim 5, wherein said crystalline polymorph is characterized by X-ray powder diffraction peaks at:

| Angle/2° |
|---|
| 7.56 |
| 15.03 |
| 17.26 |
| 17.86 |
| 18.48 |
| 19.14 |

| Angle/2° |
|---|
| 19.94 |
| 20.42 |
| 21.62 |
| 22.44 |
| 22.82 |
| 23.83 |
| 24.87 |
| 26.09 |
| 28.59 |
| 29.41. |

7. A crystalline polymorph of an HBr salt of a compound of Formula I:

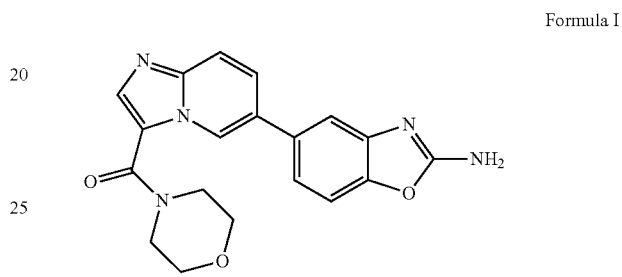

Formula I wherein said crystalline polymorph is HBr Pattern 2 characterized by X-ray powder diffraction peaks at 9.1 (±0.4) degrees, 17.3 (±0.4) degrees, 21.1 (±0.4) degrees, and 27.2 (±0.4) degrees two theta.

8. The crystalline polymorph of claim 7, wherein said crystalline polymorph is characterized by X-ray powder diffraction peaks at:

| Angle/2° |
|---|
| 9.11 |
| 11.37 |
| 14.86 |
| 15.98 |
| 17.30 |
| 18.52 |
| 19.72 |
| 20.33 |
| 21.08 |
| 22.29 |
| 22.35 |
| 23.31 |
| 24.87 |
| 25.38 |
| 26.53 |
| 27.22 |
| 28.59. |

9. A pharmaceutical composition comprising a therapeutically effective amount of a crystalline polymorph of claim 1 or 2.

* * * * *